(12) United States Patent
Araki et al.

(10) Patent No.: US 8,883,947 B2
(45) Date of Patent: Nov. 11, 2014

(54) METHOD OF FORMING THIN FILM

(71) Applicant: Daikin Industries, Ltd., Osaka (JP)

(72) Inventors: Takayuki Araki, Settsu (JP); Tetsuhiro Kodani, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 13/874,285

(22) Filed: Apr. 30, 2013

(65) Prior Publication Data

US 2013/0237677 A1  Sep. 12, 2013

Related U.S. Application Data

(60) Division of application No. 12/641,183, filed on Dec. 17, 2009, now Pat. No. 8,450,439, which is a division of application No. 11/231,992, filed on Sep. 22, 2005, now Pat. No. 7,655,742, which is a continuation-in-part of application No. PCT/JP2004/004028, filed on Mar. 24, 2004.

(30) Foreign Application Priority Data

Mar. 26, 2003 (JP) ................................. 2003-086179
Dec. 19, 2003 (JP) ................................. 2003-422989

(51) Int. Cl.
*C08F 14/18* (2006.01)

(52) U.S. Cl.
USPC ......... 526/255; 428/421; 428/422; 526/348.1

(58) Field of Classification Search
USPC ........................ 526/255, 348.1; 428/421, 422
See application file for complete search history.

(56) References Cited

U.S. PATENT DOCUMENTS

| | | | | |
|---|---|---|---|---|
| 4,057,660 A | * | 11/1977 | Yoshida et al. | 427/100 |
| 4,298,719 A | * | 11/1981 | Mizuno et al. | 526/255 |
| 5,925,721 A | * | 7/1999 | Saito et al. | 526/79 |
| 7,655,742 B2 | * | 2/2010 | Araki et al. | 526/255 |
| 8,450,439 B2 | * | 5/2013 | Araki et al. | 526/255 |

FOREIGN PATENT DOCUMENTS

| | | |
|---|---|---|
| DE | 100 17 492 A1 | 10/2001 |
| EP | 0 386 711 A1 | 9/1990 |
| EP | 0 508 802 A1 | 10/1992 |
| GB | 1173552 | 12/1969 |
| GB | 2 121 810 A | 1/1984 |
| GB | 2 262 100 A | 6/1993 |
| JP | 60221409 A | 11/1985 |
| JP | 3221510 A | 9/1991 |
| JP | 10212322 A | 8/1998 |
| JP | 2002-249519 A | 9/2002 |
| WO | 81/01567 | 6/1981 |

OTHER PUBLICATIONS

K. Noda, et al.; "Investigation of Ferroelectric Properties of Vinylidene Fluoride Oligomer Evaporated Films"; Materials Research Society Symposium Proceedings; Materials Research Society; vol. 748; Jan. 1, 2003; pp. 217-222; XP009115983.*

(Continued)

*Primary Examiner* — Peter D. Mulcahy
*Assistant Examiner* — Henry Hu
(74) *Attorney, Agent, or Firm* — Sughrue Mion, PLLC

(57) ABSTRACT

A vinylidene fluoride homopolymer represented by the formula (4):

$$CF_3\text{-}(A^1)\text{-}I \qquad (4)$$

wherein $A^1$ represents a structural unit of vinylidene fluoride homopolymer which includes crystal form I alone or as main component and has a number average degree of polymerization of 5 to 12.

1 Claim, 9 Drawing Sheets

(56) References Cited

OTHER PUBLICATIONS

K. Ishida, et al.; "Structural and Electronic Characterization of Epitaxially-Grown Ferroelectric Vinylidene Fluoride Oligomer Thin Films"; Materials Research Society Symposium Proceedings; Materials Research Society; vol. 600; Jan. 1, 2000; pp. 101-106; XP009115985.*

Clenn C. Apsey, Richard D. Chambers, Paolo Odello. 'Fluoro-alkene forming eliminations using antimony pentafluoride'., Journal of Fluorine Chemistry, 1996, vol. 77, pp. 127-132.

J. Guiot, B. Amcduri, B. Boutevin., 'Radical Homopoly merization of Vinylidene Fluoride Initiated by tert-Butyl Peroxypivalate., Investigation of the Microstructure by 19F and 1H NMR Spectroscopies and Mechanisms'., Macromolecules, 2002, vol. 25, pp. 8694-8707.

Makoto Hanesaka, Koji Tashiro., 'Analysis of Progression and LAM Bands Observed in Infrared and Raman Spectra of a Series of Vinylidene Fluoride Oligomers', Macromolecules, 2002, vol. 35, pp. 10210-10215.

* cited by examiner

METHOD OF FORMING THIN FILM

CROSS-REFERENCE TO RELATED APPLICATION

This application is a Divisional of U.S. application Ser. No. 12/641,183 filed Dec. 17, 2009, which is a Divisional of U.S. application Ser. No. 11/231,992 filed Sep. 22, 2005, which is a continuation-in-part of PCT international application No. PCT/JP2004/004028 filed on Mar. 24, 2004 and which claims benefit of Japanese Patent Application No. JP 2003-86179 filed Mar. 26, 2003 and Japanese Patent Application No. JP 2003-422989 filed Dec. 19, 2003. The above-noted applications are incorporated herein by reference in their entirety.

BACKGROUND OF THE INVENTION

The present invention relates to a method of forming a thin film of vinylidene fluoride homopolymer having crystal form I. The present invention also relates to a process for preparing a vinylidene fluoride homopolymer having crystal form I as main component which is used for forming the thin film. The present invention further relates to a novel vinylidene fluoride homopolymer.

Polymer type ferroelectric materials have advantages such as flexibility, light-weight, good processability and low price as compared with inorganic ferroelectric materials such as ceramics. There are known, as represented examples thereof, vinylidene fluoride polymers such as polyvinylidene fluoride (PVdF) and vinylidene fluoride/trifluoroethylene (VdF/TrFE) copolymer.

With respect to PVdF, crystal structures thereof are roughly classified into three kinds such as I-form (also said to be β-form), II-form (α-form) and III-form (γ-form). Among them, it is only I-form crystal that can sufficiently exhibit high ferroelectricity.

PVdF having a high molecular weight which is prepared by radical polymerization method forms crystal form II and does not exhibit ferroelectricity as it is. In order to convert crystal form II of PVdF to crystal form I, there are required complicated post-steps such as stretching and heat-treating of a film or rapid cooling under high pressure at casting.

Matsushige et al have studied formation of thin film of vinylidene fluoride oligomer having crystal form I by using vinylidene fluoride oligomer: $CF_3(CH_2CF_2)_nI$ (number average degree of polymerization n=17) having crystal form II, and in this study, have found that a thin film of vinylidene fluoride oligomer of crystal form I was formed only by deposition coating on a KBr substrate at a substrate temperature Ts>0° C., for example, at 25° C. Also it was found that in deposition-coating on a KCl substrate at 25° C., a coating film containing a mixture of crystals of I-form and II-form was formed and was almost converted to a thin film of vinylidene fluoride oligomer of crystal form I by heat-treating (at a temperature of not less than 110° C.) after the coating. However, in a substrate ($SiO_2$, Pt, Au, or the like) having small interaction with vinylidene fluoride oligomer, just after the vapor deposition and further even after the following heat treatment, only thin films containing a mixture of I- and II-form crystals have been obtained (M & BE Vol. 11, No. 2, 145 (2000).

Also Matsushige et all have recently found that a thin film of vinylidene fluoride oligomer of crystal form I could be formed on various substrates by vapor deposition of vinylidene fluoride oligomer of crystal form II under extremely low temperature environment of not more than −130° C. (Polymer Preprint, Japan, Vol. 51, No. 12, 3097 (2002)).

As mentioned above, thin films of I-form crystal have not been formed only by coating at room temperature except coating on KBr substrate.

By the way, there are various known processes for preparing polymers using vinylidene fluoride monomer.

Okui et all have made analysis of crystal structure with respect to vinylidene fluoride oligomer: $CCl_3(CH_2CF_2)_nCl$ (number average degree of polymerization n=9) prepared by radical polymerization by using $CCl_4$ as a chain transfer agent (telogen) and dinormalperoxy dicarbonate as a catalyst, and have reported that this oligomer was a mixture of crystal form I (β-form) and crystal form III (γ-form) and had a crystalline melting point Tm at two points (74° C. and 110° C.) (Polymer Journal, Vol. 30, No. 8, pp. 659 to 663 (1998), and POLYMER Vol. 38, No. 7, pp. 1677 to 1683 (1997)).

In the mentioned process for preparing vinylidene fluoride oligomer by using $CCl_4$ as a chain transfer agent (telogen), a molecular weight distribution of the obtained vinylidene fluoride oligomer is wide, and even if crystal forms I (β-form) are obtained, the crystal structures easily become a mixture of I-form (β-form) with II-form (α-form) and III-form (γ-form) and a purity of crystal form I (β-form) becomes low, which lowers ferroelectric characteristics of thin films formed by using the obtained vinylidene fluoride oligomer.

For example, "iodine transfer polymerization process" using perfluoroalkyl iodide as a chain transfer agent (or telogen) is known, and a molecular weight distribution of high molecular weight polymer can be made narrow particularly in non-crystalline polymers used for fluorine-containing rubbers or the like such as vinylidene fluoride/hexafluoropropene copolymer and vinylidene fluoride/tetrafluoroethylene/hexafluoropropene copolymer (Kobunshi Ronbunshu, 49(10), No. 10, pp. 765 to 783 (1992)).

In addition, there are known other polymerization processes such as a polymerization process not using a chain transfer agent and a polymerization process using a hydrocarbon chain transfer agent (telogen) such as isopentane or alcohol. However there is a problem that a molecular weight distribution of the obtained polymer becomes wide, and a purity of crystal form I (β-form) is lowered like the above-mentioned preparation processes.

Also with respect to polymerization processes for a low molecular weight vinylidene fluoride polymer, there are disclosed a process using, as a telogen, the same perfluoroalkyl iodide as above (JP56-57811A), a process using alcohols as a telogen (JP59-117503A), a process using perfluoroalkyl bromide as a telogen (JP63-93736A, JP7-179523A), and the like.

However all of those preparation processes are intended to prepare vinylidene fluoride copolymers (copolymer oligomers), and studies on vinylidene fluoride homopolymers (homopolymer oligomers) having crystallinity have not been made. Furthermore there are disclosed no processes for efficiently preparing, at high purity, vinylidene fluoride homopolymers having crystal form I (β-form) which can exhibit ferroelectric characteristics.

SUMMARY OF THE INVENTION

The first object of the present invention is to provide a method of forming a thin film of vinylidene fluoride homopolymer having crystal form I which is applicable to various substrates in a relatively easy manner (coating conditions, application method, etc.).

The second object of the present invention is to provide a process for preparing a vinylidene fluoride homopolymer having crystal form I efficiently at high purity.

The third object of the present invention is to provide novel vinylidene fluoride homopolymers.

The present inventors have made intensive studies and as a result, obtained vinylidene fluoride homopolymer having crystal form I directly by polymerization. The present inventors have further found that a thin film of vinylidene fluoride homopolymer having crystal form I which can exhibit ferroelectricity, can be formed on various substrates by using the obtained vinylidene fluoride homopolymer having crystal form I even by usual coating method or coating conditions, for example, on a silicon wafer by spin coating at room temperature.

Also in the study on a process for preparing vinylidene fluoride homopolymer, the present inventors have found that a vinylidene fluoride homopolymer having crystal form I can be obtained at high purity by using a specific iodine compound as a chain transfer agent (telogen) and controlling a number average degree of polymerization within a specific range.

Namely, the first of the present invention relates to a method of forming a thin film comprising vinylidene fluoride homopolymer which comprises the following steps (i) and (ii).

Step (i)

A step for preparing a green powder product of vinylidene fluoride homopolymer comprising crystal form I alone or as main component by subjecting vinylidene fluoride to radical polymerization in the presence of a bromine compound or iodine compound having 1 to 20 carbon, atoms which contains at least one moiety represented by the formula (1):

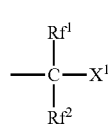

(1)

wherein $X^1$ is iodine atom or bromine atom; $Rf^1$ and $Rf^2$ are the same or different and each is selected from fluorine atom or perfluoroalkyl groups having 1 to 5 carbon atoms.

Step (ii)

A step for forming a thin film on a substrate surface by using vinylidene fluoride homopolymer which comprises crystal form I alone or as main component and is obtained from the green powder product of vinylidene fluoride homopolymer comprising crystal form I alone or as main component.

The method of forming a thin film of the present invention may further include a step (iii) for heat-treating the thin film of vinylidene fluoride homopolymer at a temperature of not less than 50° C. and lower than a crystalline melting point of the vinylidene fluoride homopolymer.

Also the method of forming a thin film of the present invention may further include a step (iv) for polarization treatment of the thin film of vinylidene fluoride homopolymer.

It is preferable that the bromine compound or iodine compound which contains the moiety of the formula (1) is a perhalo compound, and particularly in the formula (1), $X^1$ is iodine atom.

Further it is preferable that in the formula (1), both of $Rf^1$ and $Rf^2$ are fluorine atoms.

Examples of the compound which contains the moiety of the formula (1) are iodine compounds represented by the formula (2):

$$X^2-(CF_2)_n-I \quad (2)$$

wherein $X^2$ is a fluorine atom or iodine atom, n is an integer of 1 to 20.

In the vinylidene fluoride homopolymers comprising crystal form I alone or as main component, when attention is given to proportions of the respective vinylidene fluoride homopolymers having crystal form I, II or III in the green powder product of vinylidene fluoride homopolymer which are calculated by IR analysis, it is preferable that the proportion of vinylidene fluoride homopolymers having crystal form I satisfies both of (Equation 1):

$$100 \geq \text{I-form}/(\text{I-form}+\text{II-form}) \geq 50\% \text{ by weight} \quad \text{(Equation 1)}$$

and (Equation 2):

$$100 \geq \text{I-form}/(\text{I-form}+\text{III-form}) \geq 50\% \text{ by weight} \quad \text{(Equation 2).}$$

and it is further preferable that the proportion of vinylidene fluoride homopolymers having crystal form I satisfies both of (Equation 3):

$$100 \geq \text{I-form}/(\text{I-form}+\text{II-form}) \geq 70\% \text{ by weight} \quad \text{(Equation 3)}$$

and (Equation 4):

$$100 \geq \text{I-form}/(\text{I-form}+\text{III-form}) \geq 70\% \text{ by weight} \quad \text{(Equation 4).}$$

It is preferable that a number average degree of polymerization of the green powder product of vinylidene fluoride homopolymer comprising crystal form I alone or as main component is from 4 to 15.

The step (ii) for forming a thin film of vinylidene fluoride homopolymer may be carried out by applying a liquid composition containing the vinylidene fluoride homopolymer on a substrate surface or by vacuum vapor deposition of composition containing the vinylidene fluoride homopolymer on a substrate surface.

It is preferable that the step (ii) for forming a thin film of vinylidene fluoride homopolymer is carried out at a temperature of not less than 10° C. and lower than a crystalline melting point of the vinylidene fluoride homopolymer.

The thin film of vinylidene fluoride homopolymer may be formed on a surface of silicon substrate or on a surface of metallic substrate, for example, on a surface of at least one selected from the group consisting of aluminum, copper, gold, silver and platinum.

The vinylidene fluoride homopolymer comprising crystal form I alone or as main component can be formed into a thin film on a substrate surface in a thickness of 0.1 to 1,000 nm.

The second of the present invention relates to a process for preparing a vinylidene fluoride homopolymer which comprises crystal form I alone or as main component and has a number average degree of polymerization of 4 to 15, in which vinylidene fluoride is subjected to radical polymerization in the presence of a radical polymerization initiator and at least one of perfluoro iodides represented by the formula (2):

$$X^2-(CF_2)_n-I \quad (2)$$

wherein $X^2$ is a fluorine atom or iodine atom, n is an integer of 1 to 20.

In such a preparation process, it is preferable that the perfluoro iodide of the formula (2) is $CF_3I$ or is one represented by the formula (3):

$$I-(CF_2CF_2)_{n1}-I \quad (3)$$

wherein n1 is an integer of 1 to 5.

According to such a preparation process, the number average degree of polymerization of the vinylidene fluoride homopolymer comprising crystal form I as main component can be adjusted to 5 to 12.

Particularly there can be prepared the vinylidene fluoride homopolymer comprising crystal form I alone or as main component, in which when attention is given to proportions of the respective vinylidene fluoride homopolymers having crystal form I, II or III which are calculated by IR analysis, the proportion of vinylidene fluoride homopolymers having crystal form I satisfies both of the above-mentioned (Equation 1) and (Equation 2) and further both of the above-mentioned (Equation 3) and (Equation 4).

The third of the present invention relates to a novel vinylidene fluoride homopolymer represented by the formula (4):

$$CF_3\text{-}(A^1)\text{-}I \qquad (4)$$

wherein $A^1$ represents a structural unit of vinylidene fluoride homopolymer which comprises crystal form I alone or as main component and has a number average degree of polymerization of 5 to 12, and a novel vinylidene fluoride homopolymer represented by the formula (5):

$$I\text{-}(A^2)\text{-}(CF_2CF_2)_m\text{-}(A^3)\text{-}I \qquad (5)$$

wherein m is an integer of 1 to 5; $A^2$ and $A^3$ are the same or different and each is a structural unit of vinylidene fluoride homopolymer comprising crystal form I alone or as main component; the sum of number average degree of polymerization of the structural units $A^2$ and $A^3$ is 2 to 20, particularly 4 to 15.

Further particularly useful as the novel vinylidene fluoride homopolymer are vinylidene fluoride homopolymers comprising crystal form I alone or as main component, in which when attention is given to proportions of the respective vinylidene fluoride homopolymers having crystal form I, II or III which are calculated by IR analysis, the proportion of vinylidene fluoride homopolymers having crystal form I satisfies both of the above-mentioned (Equation 1) and (Equation 2) and further both of the above-mentioned (Equation 3) and (Equation 4).

DETAILED DESCRIPTION

Figure 1:
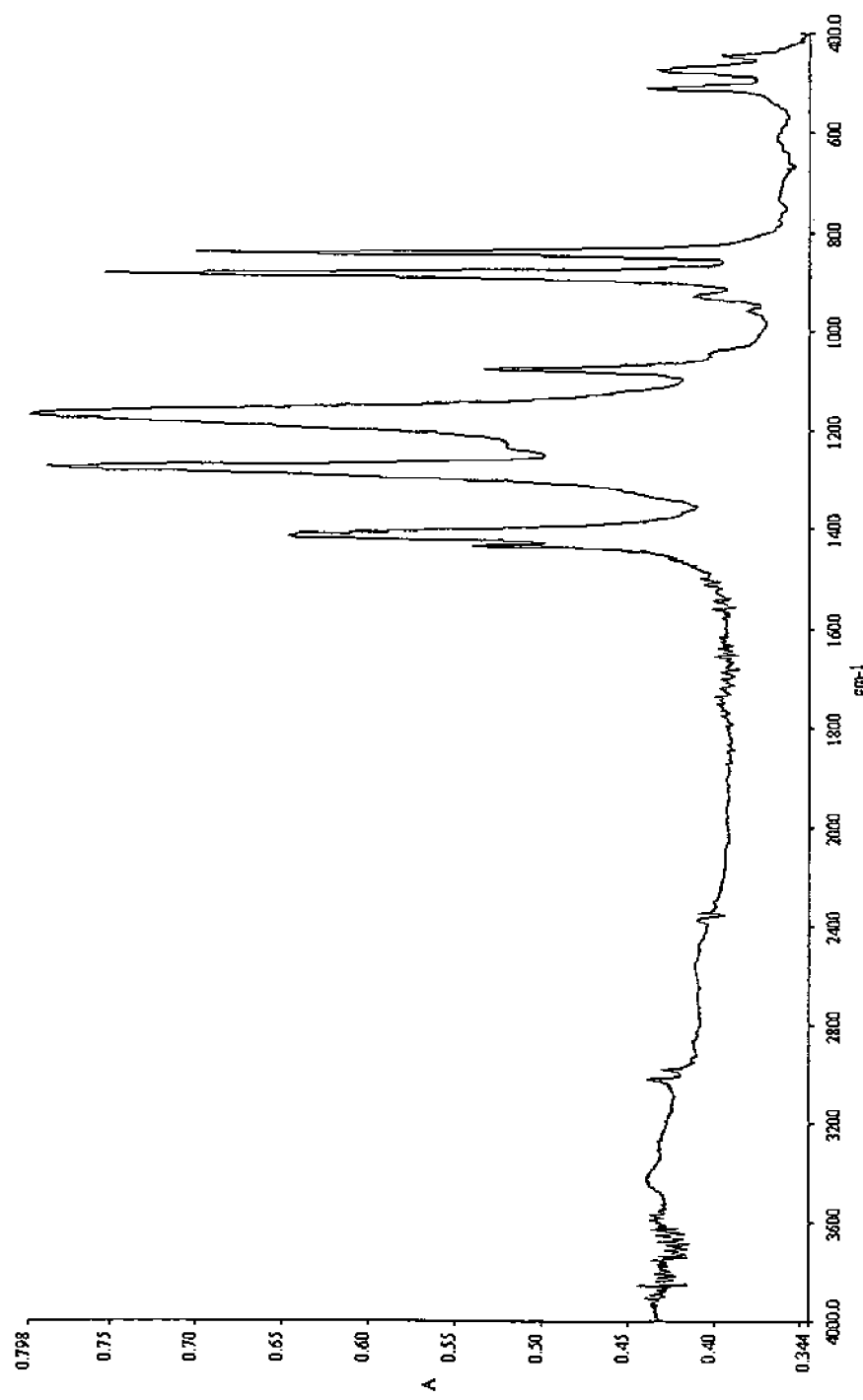
FIG. 1 is an IR chart of vinylidene fluoride homopolymer of all-I-form crystal structure.

Next, the present invention is explained concretely,

Firstly, the first of the present invention relates to, as mentioned above, the method of forming a thin film comprising vinylidene fluoride homopolymer which comprises the following steps (i) and (ii).

Step (i)

A step for preparing a green powder product of vinylidene fluoride homopolymer comprising crystal form I alone or as main component by subjecting vinylidene fluoride to radical polymerization in the presence of a bromine compound or iodine compound having 1 to 20 carbon atoms which contains at least one moiety represented by the formula (1):

wherein $X^1$ is iodine atom or bromine atom; $Rf^1$ and $Rf^2$ are the same or different and each is selected from fluorine atom or perfluoroalkyl groups having 1 to 5 carbon atoms.

Step (ii)

A step for forming a thin film on a substrate surface by using vinylidene fluoride homopolymer which comprises crystal form I alone or as main component and is obtained from the green powder product of vinylidene fluoride homopolymer comprising crystal form I alone or as main component.

The method of the present invention is preferred because the vinylidene fluoride homopolymer can be applied to not only specific substrates such as KBr and KCl but also any other substrates and also because coating can be easily carried out under usual coating conditions even without setting any special coating conditions such as very low temperatures.

As a result, the thin film obtained by the method of the present invention comprises vinylidene fluoride homopolymer comprising crystal form I, and possesses capability of exhibiting ferroelectricity when subjected to polarization treatment or the like.

The vinylidene fluoride homopolymer which is used for forming a thin film of the present invention comprises crystal form I alone or as main component. When attention is given particularly to the respective vinylidene fluoride homopolymers having crystal form I, II or III, it is preferable that the vinylidene fluoride homopolymers having crystal form I are present in a ratio higher than those of the vinylidene fluoride homopolymers having crystal form II and vinylidene fluoride homopolymers having crystal form III.

The crystal form I of vinylidene fluoride homopolymer is characterized in that a fluorine atom bonded to one carbon atom of the trunk chain in the polymer molecule and a hydrogen atom bonded to the neighboring carbon atom take a trans conformation (TT conformation), namely, the fluorine atom and hydrogen atom bonded to the neighboring carbon atoms are positioned oppositely at an angle of 180° when viewing from the carbon-carbon bond.

In the present invention, the vinylidene fluoride homopolymer having crystal form I may take the TT conformation in the whole of one polymer molecule or in a part of the polymer molecule, and has the molecular chain of the TT conformation in at least four continuous vinylidene fluoride monomer units. In any cases, the carbon-carbon bond, in which the TT conformation constitutes the TT trunk chain, has a planar zigzag structure, and the dipole moments of C—$F_2$ and C—$H_2$ bonds have moieties in the vertical direction to the molecular chain. When the vinylidene fluoride homopolymer having crystal form I is subjected to IR analysis, there are characteristic peaks (characteristic absorptions) around 1,274 $cm^{-1}$, 1,163 $cm^{-1}$ and 840 $cm^{-1}$. In powder X-ray diffraction analysis, there is a characteristic peak around 2θ=21°.

In the IR analysis, when characteristic absorptions of crystal form I are recognized but characteristic absorptions of crystal forms II and III are not recognized substantially, the crystal structure is called "all-I-form crystal structure".

The crystal form II of vinylidene fluoride homopolymer is characterized in that to a fluorine atom (or hydrogen atom) bonded to one carbon atom of trunk chain in the polymer molecule, a hydrogen atom (or fluorine atom) bonded to one neighboring carbon atom takes a trans form, and a hydrogen atom (or fluorine atom) bonded to another (opposite) neighboring carbon atom takes a gauche form (positioned at an angle of 60°), and there are two or more continuous chains of this conformation. (TG$\overline{\text{TG}}$ conformation). The molecular chain is of TG$\overline{\text{TG}}$ type and the dipole moments of C—$F_2$ and C—$H_2$ bonds have respective moieties in both of the vertical and horizontal directions to the molecular chain. When the vinylidene fluoride homopolymer having crystal form II is subjected to IR analysis, there are characteristic peaks (characteristic absorptions) around 1,212 $cm^{-1}$, 1,183 $cm^{-1}$ and 762 $cm^{-1}$. In powder X-ray diffraction analysis, there are characteristic peaks around 2θ=17.7°, 18.3° and 19.9°.

In the IR analysis, when characteristic absorptions of crystal form II are recognized but characteristic absorptions of crystal forms I and III are not recognized substantially, the crystal structure is called "all-II-form crystal structure".

The crystal form III of vinylidene fluoride homopolymer is characterized by having a conformation (T3GT3$\overline{\text{G}}$ conformation) comprising TT conformation and TG conformation alternately continuously. The molecular chain is of $T_3GT_3\overline{G}$ type and the dipole moments of C—$F_2$ and C—$H_2$ bonds have respective moieties in both of vertical and horizontal directions to the molecular chain. When the vinylidene fluoride homopolymer having crystal form III is subjected to IR analysis, there are characteristic peaks (characteristic absorptions) around 1,235 $cm^{-1}$ and 811 $cm^{-1}$. In powder X-ray diffraction analysis, there is a characteristic peak around 2θ=18°.

Usually the presence of crystal form III is recognized in the form of a mixture with the crystal form I and/or the crystal form II.

In the present invention, "comprising the crystal form I as main component" means preferably that the proportion of vinylidene fluoride homopolymers having crystal form I satisfies both of the following (Equation 1) and (Equation 2).

100≥I-form/(I-form+II-form)≥50% by weight (Equation 1)

100≥I-form/(I-form+III-form)≥50% by weight (Equation 2).

The presence and proportions of vinylidene fluoride homopolymers having crystal form I, II or III can be analyzed by various methods such as X-ray diffraction method and IR analysis method. In the present invention, the content F(I) of crystal form I in the vinylidene fluoride homopolymer is calculated from a peak height (absorbance A) of characteristic absorption of each crystal structure in an IR analysis chart by the following methods.

(1) Calculation of content (% by weight, F(I)×100) of I-form in a mixture of I-form and II-form
(1-1) Equation Law of Beer: $A = \epsilon bC$ wherein A represents an absorbance, E represents a molar extinction coefficient, b represents an optical path length, and C represents a concentration. When an absorbance of characteristic absorption of crystal form I is assumed to be $A^I$, an absorbance of characteristic absorption of crystal form II is assumed to be $A^{II}$, a molar extinction coefficient of crystal form I is assumed to be $\epsilon^I$, a molar extinction coefficient of crystal form II is assumed to be $\epsilon^{II}$, a concentration of crystal form I is assumed to be $C^I$ and a concentration of crystal form II is assumed to be $C^{II}$, the following equation is obtained.

$$A^I/A^{II} = (\epsilon^I/\epsilon^{II}) \times (C^I/C^{II}) \tag{1a}$$

When a correction factor ($\epsilon^I/\epsilon^{II}$) of the molar extinction coefficient is assumed to be $E^{I/II}$, the content F(I) ($=C^I/C^{II}$)) of crystal form I is represented by the following equation.

$$F(I) = \frac{\frac{1}{E^{I/II}} \times \frac{A^{II}}{A^I}}{1 + \frac{1}{E^{I/II}} \times \frac{A^{II}}{A^I}} = \frac{A^I}{E^{I/II}A^{II} + A^I} \tag{2a}$$

Therefore when the correction factor $E^{I/II}$ is decided, the content F(I) of crystal form I can be calculated from a measured absorbance $A^I$ of characteristic absorption of form I and a measured absorbance $A^{II}$ of characteristic absorption of crystal form II.

(1-2) Method of deciding correction factor $E^{I/II}$

Figure 2:
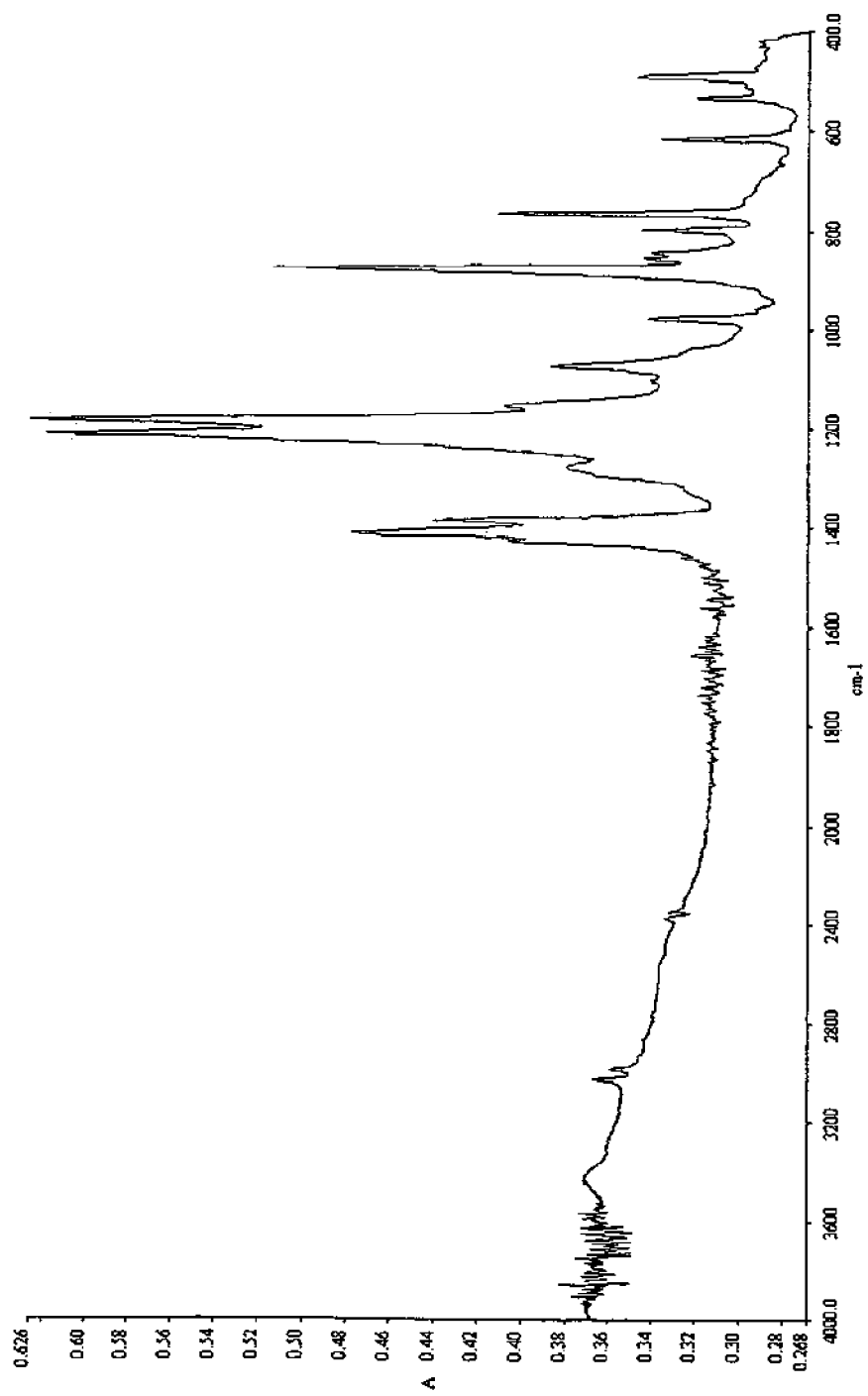
FIG. 2 is an IR chart of vinylidene fluoride homopolymer of all-II-form crystal structure.
Figure 3:
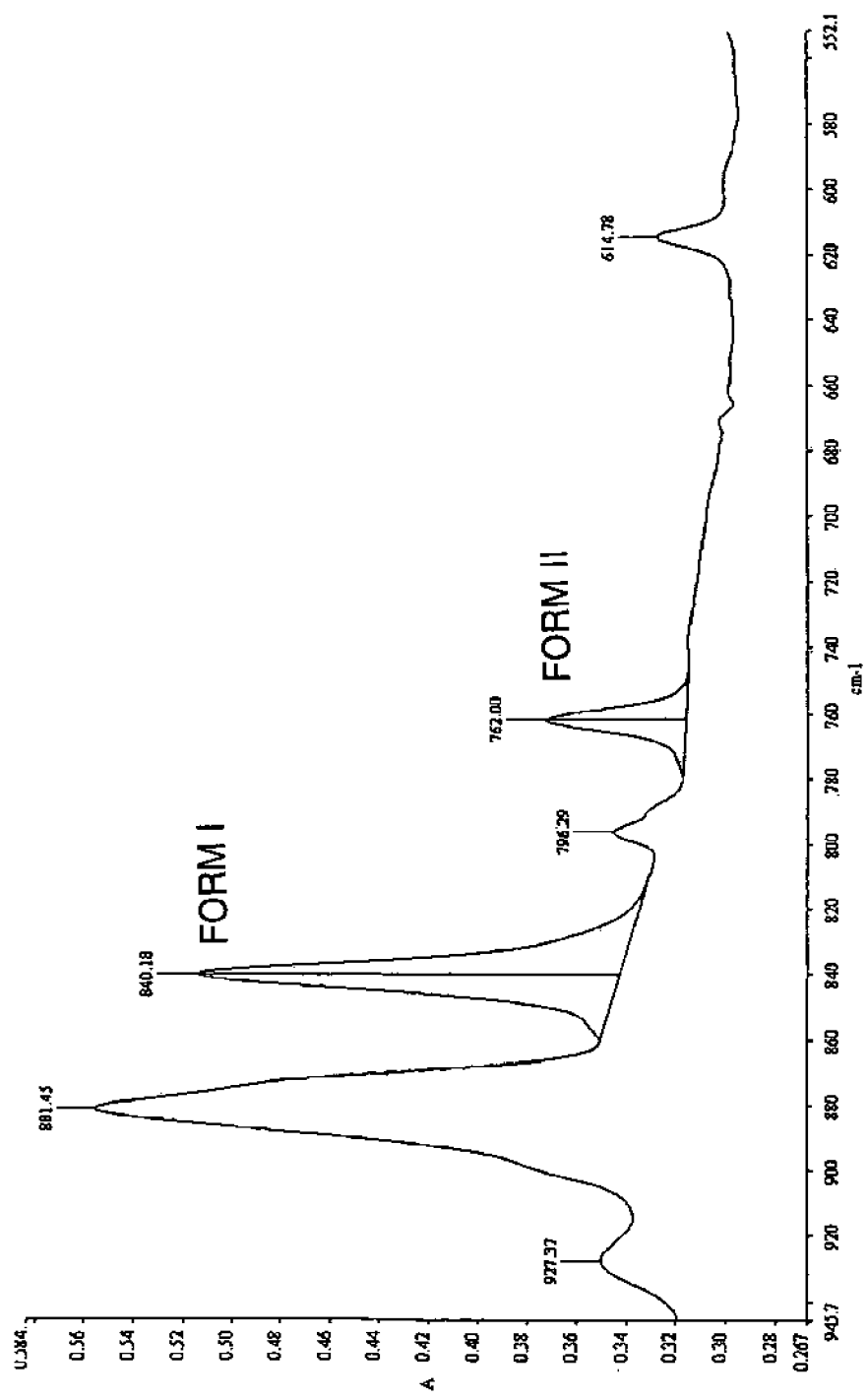
FIG. 3 is an IR chart of vinylidene fluoride homopolymer comprising a mixture of crystal forms I and II for explaining a method of reading peak heights of characteristic absorption of crystal forms I and II.

A sample in which the content F(I) of crystal form I is known is prepared by mixing a sample of all-I-form crystal structure (FIG. 1) and a sample of all-II-form crystal structure (FIG. 2), and is subjected to IR analysis. (peak height) $A^I$ and $A^{II}$ of each characteristic absorption are read from the obtained chart (FIG. 3).

Then the absorbances are substituted in Equation (3a) obtained from Equation (2a):

$$E^{I/II} = \frac{A^I \times (1 - F(I))}{A^{II} \times F(I)} \tag{3a}$$

and the correction factor $E^{I/II}$ is obtained. By changing the mixing ratio of the samples repeatedly, each correction factor $E^{I/II}$ is obtained, and an average value of 1.681 is obtained.

As a characteristic absorption of crystal form 1,840 $cm^{-1}$ of is used (Reference bulletin: Bachmann et al., Journal of Applied Physics, Vol. 50, No. 10 (1979)), and 763 $cm^{-1}$ referred to in the mentioned bulletin is used as a characteristic absorption of crystal form II.

(2) Content F(I) of I-form in a mixture of I-form and III-form

Since a substance consisting of crystal form III is difficult to obtain, a mixture of II-form and III-form is used as a standard substance.

Figure 4:
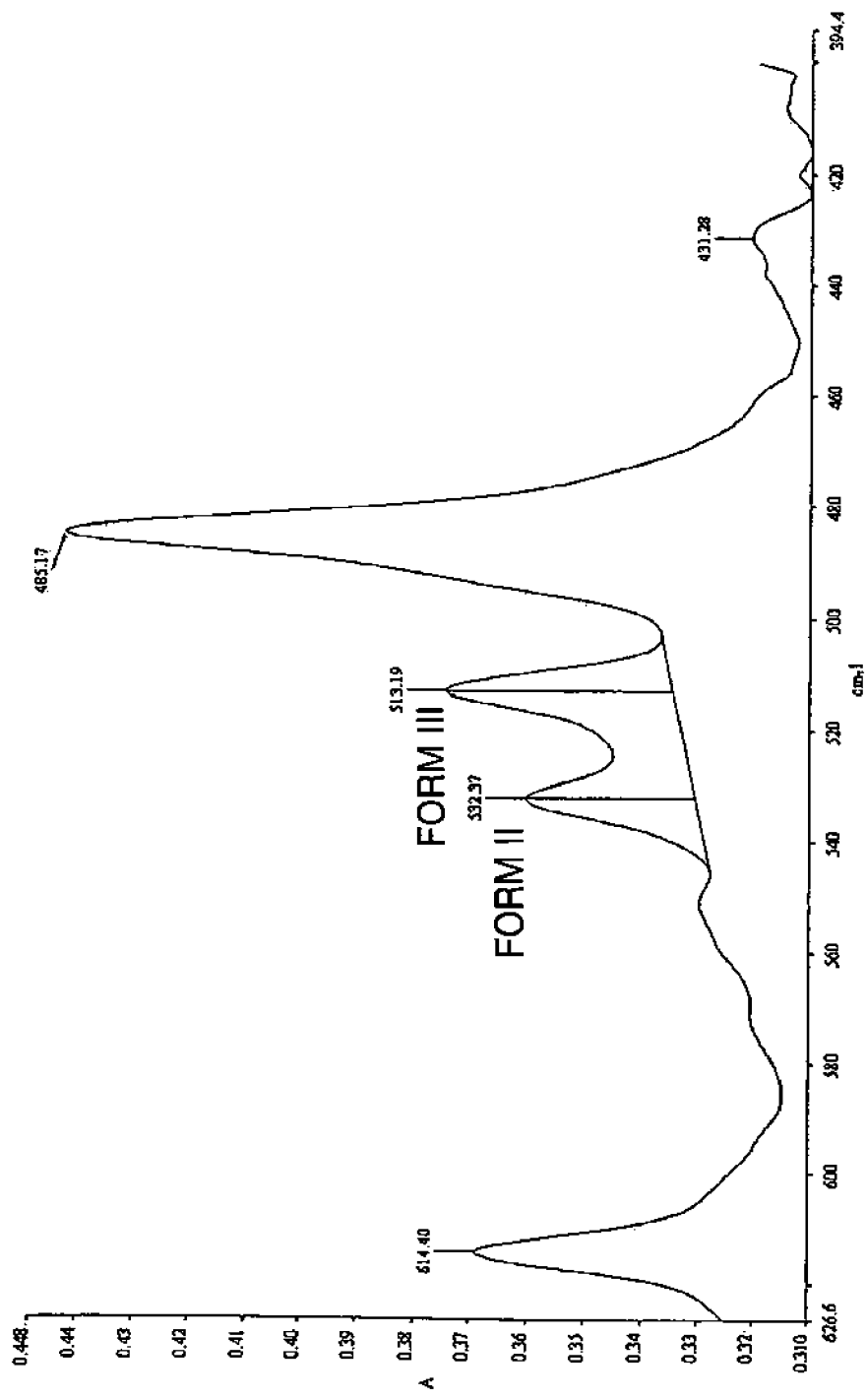
FIG. 4 is an IR chart of vinylidene fluoride homopolymer comprising a mixture of crystal forms II and III for explaining a method of reading peak heights of characteristic absorption of crystal forms II and III.

(2-1) Firstly, in the mentioned equation (2a), $A^I$ and $A^{II}$ are assumed to be $A^{II}$ and $A^{III}$, respectively and the correction factor $E^{II/III}$ of the mixture of II-form and III-form is assumed to be 0.81 from the bulletin (S. Osaki et al., Journal of Polymer Science: Polymer Physics Edition, Vol. 13, pp. 1071 to 1083 (1975). The content of crystal form III in the standard mixture of II-form and III-form is calculated by substituting $A^{II}$ and $A^{III}$ which are read from the IR chart (FIG. 4) of the standard mixture of II-form and III-form, in the equation (F(III)=0.573). As a characteristic absorption of crystal form III, 811 cm$^{-1}$ is used (Reference bulletin: Bachmann et al., Journal of Applied Physics, Vol. 50, No. 10 (1979)).

Figure 5:
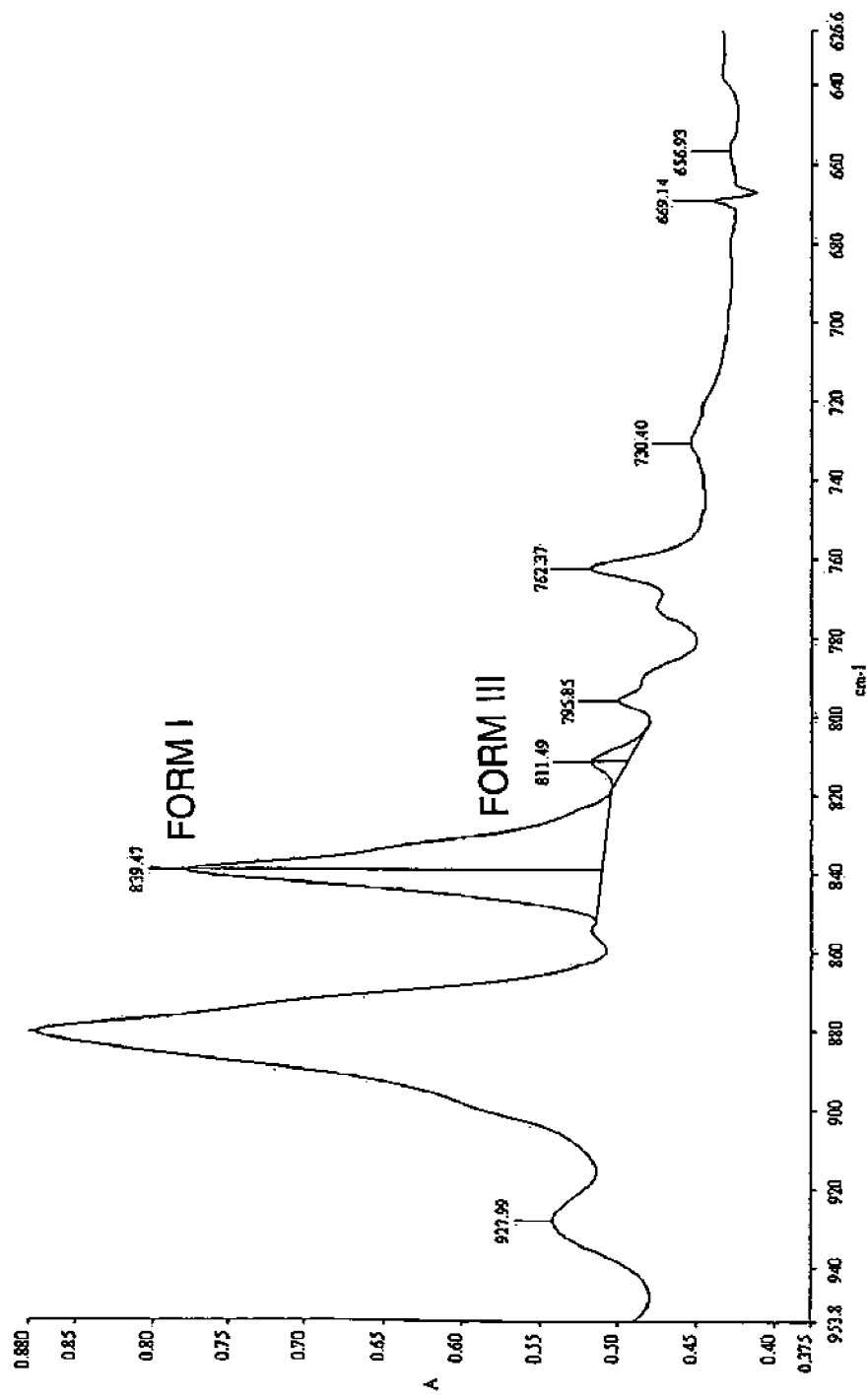
FIG. 5 is an IR chart of vinylidene fluoride homopolymer comprising a mixture of crystal forms I, II and III, in which a content F(I) of crystal form I is known, for explaining a method of reading peak heights of characteristic absorption of crystal forms I and III.

(2-2) Next, the standard mixture of II-form and III-form in which the content of III-form is known is mixed with a substance of all-I-form crystal structure in a specific ratio to prepare a mixture of I-form, II-form and III-form, in which the content of I-form is known. This mixture is subjected to IR analysis and $A^I$ and $A^{II}$ are read from the chart (FIG. 5) and the correction factor $E^{I/III}$ ($\in^I/\in^{III}$) is calculated from the mentioned equation (3a) ($A^{II}$ is changed to $A^{III}$). By changing the mixing ratio of the standard mixture of II-form and III-form and the substance of I-form repeatedly, each correction factor $E^{I/III}$ is obtained, and an average value of 6.758 is obtained.

(2-3) By using this correction factor $E^{I/III}$=6.758, the content F(I) of I-form in the mixture of I-form and III-form is obtained from the mentioned equation (2a) ($A^{II}$ is changed to $A^{III}$).

Preferred vinylidene fluoride homopolymers used in the method of forming a thin film of the present invention are those satisfying both of the following equations:

100≥I-form/(I-form+II-form)≥60% by weight and

100≥I-form/(I-form+III-form)≥60% by weight and more preferably those satisfying both of (Equation 3) and (Equation 4).

100≥I-form/(I-form+II-form)≥70% by weight    (Equation 3)

100≥I-form/(I-form+III-form)≥70% by weight    (Equation 4).

Further preferred are those satisfying both of the following equations:

100≥I-form/(I-form+II-form)≥80% by weight and

100≥I-form/(I-form+III-form)≥80% by weight.

Those are preferred since high ferroelectricity can be exhibited by polarization treatment.

Further the proportion of crystal form I is preferably within the range represented by the equation:

100≥I-form/(I-form+II-form+III-form)≥50% by weight, more preferably

100≥I-form/(I-form+II-form+III-form)≥70% by weight, particularly preferably

100≥I-form/(I-form+II-form+III-form)≥80% by weight.

A big feature of the present invention is that according to intensive studies on polymerization method, the vinylidene fluoride homopolymer comprising form I alone or as main component so as to satisfy the above-mentioned equations can be prepared in the form of green powder product after the polymerization even without a specific post-treatment.

First, the step (i) is explained below. In addition, the process for preparing a vinylidene fluoride homopolymer which is the second of the present invention is also referred to.

The step (i) in the method of forming a thin film of the present invention is a step for preparing a vinylidene fluoride homopolymer comprising crystal form I alone or as main component by subjecting vinylidene fluoride to radical polymerization in the presence of a bromine compound or iodine compound having 1 to 20 carbon atoms which contains at least one moiety represented by the formula (1):

(1)

wherein $X^1$ is iodine atom or bromine atom; $Rf^1$ and $Rf^2$ are the same or different and each is selected from fluorine atom or perfluoroalkyl groups having 1 to 5 carbon atoms.

Namely, when the bromine compound or iodine compound having the moiety represented by the formula (1) is used as a chain transfer agent (telogen) for the polymerization, a polymer having a narrow molecular weight distribution and a polymer chain having a low branch ratio can be synthesized, and a vinylidene fluoride homopolymer, in which the content of crystal form I is high, can be obtained.

Examples of the moiety represented by the formula (1) are:

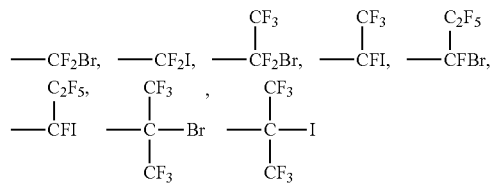

and the like. Particularly preferred are iodine compounds since a molecular weight distribution can be made narrower, and as a result, a vinylidene fluoride homopolymer, in which the content of crystal form is high, can be obtained.

Also it is preferable that in the moiety of the formula (1), $Rf^1$ and $Rf^2$ are F since a vinylidene fluoride homopolymer, in which the content of crystal form I is high, can be obtained.

Among the bromine compounds or iodine compounds having the moiety represented by the formula (1), preferred are polyfluoro compounds having the moiety of the formula (1), more preferably perfluoro compounds having the moiety of the formula (1) since polymerization reaction advances at higher yield and a polymer having a narrow molecular weight distribution and fewer branched chains can be obtained.

Particularly preferred is at least one of perfluoro iodides represented by the formula (2):

$$X^2-(CF_2)_n-I \quad (2)$$

wherein $X^2$ is a fluorine atom or iodine atom, n is an integer of 1 to 20, or perfluoro bromides obtained by replacing the iodine atom in the above formula (2) by bromine atom.

Examples of the perfluoro compounds are, for instance, iodine compounds such as perfluoro monoiodide compounds such as monoiodide perfluoromethane, monoiodide perfluoroethane, monoiodide perfluoropropane, monoiodide perfluorobutane (for example, 2-iodide perfluorobutane, 1-iodide perfluoro(1,1-dimethylethane)), monoiodide perfluoropentane (for example, 1-iodide perfluoro(4-methylbutane)), 1-iodide perfluoro-n-nonane, monoiodide perfluorocyclobutane, 2-iodide perfluoro(1-cyclobutyl)ethane and monoiodide perfluorocyclohexane; perfluoro diiodide compounds such as diiodide perfluoromethane, 1,2-diiodide perfluoroethane, 1,3-diiodide perfluoro-n-propane, 1,4-diiodide perfluoro-n-butane, 1,7-diiodide perfluoro-n-octane, 1,2-di(iodidedifluoromethyl)perfluorocyclobutane and 2-iodide1,1,1-trifluoroethane, and bromine compounds obtained by replacing the iodine atoms of those iodine compounds by bromine atoms.

The second of the present invention is the process for preparing, under relatively easy conditions, a vinylidene fluoride homopolymer containing crystal form I at higher purity by selecting a specific perfluoro iodide represented by the formula (2) among the above-mentioned chain transfer agents (telogen) and adjusting to a specific number average degree of polymerization.

Concretely the preparation of vinylidene fluoride homopolymer comprising crystal form I alone or as main component is characterized in that the radical polymerization is carried out in the presence of a radical polymerization initiator and at least one of perfluoro iodides represented by the formula (2):

$$X^2—(CF_2)_n—I \qquad (2)$$

wherein $X^2$ is a fluorine atom or iodine atom, n is an integer of 1 to 20, and a number average degree of polymerization of vinylidene fluoride units in the polymer is adjusted to 4 to 20, preferably 4 to 15, thereby assuring the preparation of the homopolymer.

Namely, it is important to use an iodine compound having a linear fluoroalkyl group, which makes it easier to prepare a polymer having a high purity of crystal form I as compared with use of a branched fluoroalkyl group such as $(CF_3)_2CF—I$.

In the iodine compounds of the formula (2), it is more preferable that n is 1 or 4m, in which m is 1 to 5.

Examples of the iodine compounds of the formula (2) are, for instance, $CF_3I$, $F(CF_2)_4I$, $F(CF_2)_8I$ and in addition, perfluoro diiodides represented by $I(CF_2CF_2)_{n1}I$, in which n1 is an integer of 1 to 5 [for example, $I(CF_2CF_2)I$, $I(CF_2CF_2)_2I$, $I(CF_2CF_2)_3I$, $I(CF_2CF_2)_4I$ and the like]. Particularly preferred are $CF_3I$ and $I(CF_2CF_2)_{n1}I$, in which n1 is an integer of 1 to 5, and among them, $CF_3I$ and $I(CF_2CF_2)_2I$ are preferred.

When those iodine compounds are used as a chain transfer agent (telogen), the vinylidene fluoride homopolymer of crystal form I can be obtained at high purity in high efficiency.

When attention is given to recurring units of only vinylidene fluoride in the vinylidene fluoride homopolymer, a lower limit of number average degree of polymerization thereof is preferably 4, particularly preferably 5, and an upper limit thereof is preferably 20, more preferably 15, further preferably 12, particularly preferably 10. Too high number average degree of polymerization is not preferred because a ratio of crystal form I is decreased.

In the present invention, the preparation of vinylidene fluoride homopolymer is carried out by radical reaction of vinylidene fluoride in the presence of the iodine compound mentioned above. The reaction is usually initiated by contacting the vinylidene fluoride to a radical generating source.

There can be used a radical polymerization initiator, light, heat or the like as a radical generating source. Preferably the preparation is carried out in the presence of a radical polymerization initiator since a degree of polymerization can be controlled, reaction can be advanced smoothly and a high yield of polymer can be obtained.

There can be used peroxides, azo initiators and the like as the radical polymerization initiator.

Examples of peroxides are, for instance, peroxydicarbonates such as n-propylperoxy dicarbonate, i-propylperoxy dicarbonate, n-butylperoxy dicarbonate, t-butylperoxy dicarbonate and bis(4-t-butylcyclohexyl)peroxy dicarbonate; oxyperesters such as α,α'-bis(neodecanoylperoxy)diisopropylbenzene, cumylperoxyneodecanoate, 1,1,3,3-tetramethylbutyl peroxyneodecanoate, 1-cyclohexyl-1-methylethyl peroxyneodecanoate, t-hexyl peroxyneodecanoate, t-butyl peroxyneodecanoate, t-hexyl peroxypivalate, t-butyl peroxypivalate, 1,1,3,3-tetramethylbutylperoxy-2-ethylhexanoate, 2,5-dimethyl-2,5-bis(2-ethylhexanoylperoxy)hexane, t-hexylperoxy-2-ethylhexanoate, t-butylperoxy-2-ethylhexanoate, t-butylperoxy isobutyrate, t-hexylperoxy isopropyl monocarbonate, t-butylperoxy maleic acid, t-butylperoxy-3,5,5-trimethylhexanoate, t-butylperoxy laurate, 2,5-dimethyl-2,5-bis(m-toluoylperoxy) hexane, t-butylperoxy isopropyl monocarbonate, t-butylperoxy-2-ethylhexyl monocarbonate, t-hexylperoxy benzoate, 2,5-dimethyl-2,5-bis(benzoyl)hexane, t-butyl peroxyacetate, a mixture of t-butylperoxy-m-tolurate and peroxy benzoate, t-butylperoxy benzoate and di-t-butylperoxy isophthalate; diacyl peroxides such as isobutyl peroxide, 3,5,5-trimethylhexanoyl peroxide, octanoyl peroxide, lauroyl peroxide, stearoyl peroxide, succinic acid peroxide, m-toluoyl peroxide and benzoyl peroxide; peroxy ketals such as 1,1-bis(t-hexylperoxy)-3,3,5-trimethylcyclohexane, 1,1-bis(t-hexylperoxy)cyclohexane, 1,1-bis(t-butylperoxy)-3,3,5-trimethylcyclohexane, 1,1-bis(t-butylperoxy)-2-methylcyclohexane, 1,1-bis(t-butylperoxy)cyclohexane, 2,2-bis(t-butylperoxy) butane, n-butyl-4,4-bis(t-butylperoxy)valerate and 2,2-bis(4, 4-di-t-butylperoxy)cyclohexyl)propane; dialkyl peroxides such as α,α'-bis(t-butylperoxy)diisopropylbenzene, dicumyl peroxide, 2,5-dimethyl-2,5bis(t-butylperoxy)hexane, t-butylcumyl peroxide, di-t-butyl peroxide and 2,5-dimethyl-2,5bis(t-butylperoxy)hexyne-3; hydroperoxides such as p-menthane hydroperoxide, diisopropylbenzene hydroperoxide, 1,1,3,3-tetramethylbutyl hydroperoxide, cumene hydroperoxide and t-butyl hydroperoxide; persulfates such as ammonium persulfate, potassium persulfate and sodium persulfate; perchloric acids, hydrogen peroxides and the like.

Also there can be used peroxides having fluorine atom. Preferred examples thereof are one or two or more of fluorine-containing diacyl peroxides, fluorine-containing peroxy dicarbonates, fluorine-containing peroxy diesters and fluorine-containing dialkyl peroxides. Among them, preferred are difluoroacyl peroxides such as pentafluoropropionoyl peroxide $(CF_3CF_2COO)_2$, heptafluorobutyryl peroxide $(CF_3CF_2CF_2COO)_2$, 7H-dodecafluoroheptanoyl peroxide $(CHF_2CF_2CF_2CF_2CF_2CF_2COO)_2$ and the like.

Examples of the azo type radical polymerization initiator are, for instance, 2,2'-azobisisobutyronitrile, 2,2'-azobis(2,4-dimethylvaleronitrile), 2,2'-azobis(2-methylvaleronitrile) 2,2'-azobis(2-cyclopropylpropionitrile), dimethyl 2,2'-azibis(isobutyrate), 2,2'-azobis[2-(hydroxymethyl)propionitrile] and 4,4'-azobis(4-cyanopentenic acid).

Among the radical polymerization initiators, particularly preferred are peroxy dicarbonates, difluoroacyl peroxides, oxyperesters, persulfates and the like.

In the process for preparing vinylidene fluoride homopolymer of the present invention, with respect to the amount of iodine compound, a lower limit thereof to 1 mole of vinylidene fluoride monomer is 0.01 mole, preferably 0.02 mole, more preferably 0.03 mole, particularly preferably 0.08 mole, and an upper limit thereof to 1 mole of vinylidene fluoride monomer is 10 mole, preferably 6 mole, more preferably 2 mole, particularly preferably 1 mole.

If the amount of iodine compound is too small, a degree of polymerization is increased excessively and as a result, the content of crystal form I is decreased, which is not preferred. Too large amount of iodine compound is not preferred because polymerization reaction is difficult to be advanced, yield is lowered and a degree of polymerization is decreased excessively.

With respect to the amount of radical polymerization initiator, a lower limit thereof to 1 mole of iodine compound is 0.0001 mole, preferably 0.01 mole, more preferably 0.03 mole, particularly preferably 0.04 mole, and an upper limit thereof to 1 mole of iodine compound is 0.9 mole, preferably 0.5 mole, more preferably 0.1. mole, particularly preferably 0.08 mole.

Too small amount of radical polymerization initiator is not preferred because polymerization reaction is difficult to be advanced, and too large amount thereof is not preferred because the content of crystal form 1 is decreased.

In the process for preparing vinylidene fluoride homopolymer of the present invention, there can be used a method of bulk polymerization without using a polymerization solvent, a method of solution polymerization using a solvent for dissolving monomers in a polymerization system, a method of suspension polymerization using a solvent for dissolving and dispersing monomers in a polymerization system and as case demands, a dispersion medium such as water, a method of emulsion polymerization in an aqueous solvent containing an emulsifying agent and the like.

Among them, solution polymerization and suspension polymerization are preferred since the degree of polymerization is easily controlled.

Examples of the polymerization solvents which can be used for solution polymerization and suspension polymerization are ketone solvents such as acetone, methyl ethyl ketone and methyl isobutyl ketone; ester solvents such as ethyl acetate, cellosolve acetate, n-butyl acetate, isobutyl acetate, methyl cellosolve acetate and carbitol acetate; alcohol solvents such as methyl alcohol, ethyl alcohol, isopropyl alcohol, n-butyl alcohol, isobutyl alcohol, tert-butyl alcohol, sec-butyl alcohol, tert-amyl alcohol, 3-pentanol, octyl alcohol and 3-methyl-3-methoxybutanol; aromatic solvents such as benzene, toluene and xylene; and the like. Also there can be used fluorine-containing solvents such as $CHF_2CF_2OCHF_2$, $(CF_3)_2CFOCH_3$, $CF_3CF_2CF_2OCH_3$, $CHF_2CF_2OCH_3$, $CF_3CF_2CH_2OCHF_2$, $CF_3CFHCF_2OCH_3$, $CHF_2CF_2OCH_2CF_3$, $CF_3CF_2CF_2CF_2OCH_3$, $CF_3CF_2CH_2OCF_2CHF_2$, $(CF_3)_2CHCF_2OCH_3$, $CF_3CFHCF_2OCH_2CF_3$, $CF_3CF_2CF_2OCH_2CH_3$, $CF_3CHFCF_2OCH_2CF_2CF_3$, $CF_3CHFCF_2CH_2OCHF_2$, $CHF_2CF_2CH_2OCF_2CHF_2$, $CF_3CFHCF_2OCH_2CF_2CF_2H$, $CHF_2CF_2CF_2CF_2CH_2OCH_3$, $C_6F_{12}$, $C_9F_{18}$, $C_6F_{14}$, $CF_3CH_2CF_2CH_3$, $CHF_2CF_2CF_2CHF_2$, $(CF_3)_2CFCHFCHFCF_3$, $CF_3CHFCHFCF_2CF_3$, $(CF_3)_2CHCF_2CF_2CF_3$, $C_4H_2F_6$, $CF_3CF_2CHF_2$, $CF_2ClCF_2CF_2CHF_2$, $CF_3CFClCFClCF_3$, $CF_2ClCF_2CF_2CF_2Cl$, $CF_2ClCF_2CF_2CF_2CF_2CF_2CHF_2$, $CF_2ClCFClCFClCF_2Cl$, HCFC-225, HCFC-141b, $CF_2ClCF_2ClCF_2ClCFCl_2$, $H(CF_2)_2)_nH$ (n is an integer of 1 to 20), $CF_3O(C_2F_4O)_nCF_2CF_3$ (n is O or an integer of 1 to 10) and $N(C_4F_9)_3$.

Particularly preferred are fluorine-containing solvents because a degree of polymerization is easily controlled. Among them, particularly preferred are fluorine-containing solvents such as HCFC-225, HCFC-141b, $CF_2$ $ClCFClCFClCF_2Cl$, $CF_2ClCF_2Cl$, $CF_2ClCFCl_2$, $H(CF_2)_nH$ (n is an integer of 1 to 20) and $CF_3O(C_2F_4O)_nCF_2CF_3$ (n is O or an integer of 1 to 10) and $N(C_4F_9)_3$.

A polymerization temperature can be optionally selected depending on kind of radical polymerization initiator, and is usually from −10° C. to 200° C. A lower limit thereof is preferably 5° C., more preferably 10° C. and an upper limit thereof is preferably 150° C., more preferably 100° C.

The present inventors have found the novel vinylidene fluoride homopolymers, in which the content of crystal form I is particularly high, by using the above-mentioned specific chain transfer agent (for example, the chain transfer agent of the formula (2)) (the third of the present invention).

Namely, the first of the novel vinylidene fluoride homopolymers is the vinylidene fluoride homopolymer represented by the formula (4):

$$CF_3\text{-}(A^1)\text{-}I \qquad (4)$$

wherein $A^1$ is a structural unit of vinylidene fluoride homopolymer comprising crystal form I alone or as main component and having a number average degree of polymerization of 5 to 12.

This novel vinylidene fluoride homopolymer has $CF_3$ group at one end of one polymer molecule and an iodine atom at another end thereof. The structural unit $A^1$ has a recurring unit of vinylidene fluoride having a number average degree of polymerization of 5 to 12.

This polymer of the formula (4) has a particularly high purity of crystal form I.

If the number average degree of polymerization of the structural unit $A^1$ is not more than 4, crystals become difficult to be formed at room temperature, and if the number average degree of polymerization is not less than 13, a purity of crystal form I is decreased (for example, a ratio of crystal form II is increased).

Also it is particularly preferable that one end of the polymer molecule is $CF_3$ group because a purity of crystal form I is increased. For example, when one end is a long chain perfluoroalkyl group or a branched perfluoroalkyl group, a purity of crystal form I is decreased (for example, a ratio of crystal form II is increased).

This polymer of the formula (4) can be synthesized by various processes. The above-mentioned preparation process using $CF_3I$ as a chain transfer agent is preferred since a polymer having a narrow molecular weight distribution can be synthesized, and as a result, a purity of crystal form I can be increased.

A molecular weight distribution of the polymer of formula (4) varies depending on the average degree of polymerization. For example, Mw/Mn obtained by GPO analysis is not less than 1 and not more than 3, preferably not more than 2, more preferably not more than 1.5. If the molecular weight distribution is increased, a purity of crystal form I tends to be decreased.

The polymer of the formula (4) may be constructed only by polymer molecules of the formula (4-1):

$$CF_3\text{—}(CH_2CF_2)_n\text{—}I \qquad (4\text{-}1)$$

in which the vinylidene fluoride units face toward the same direction in one polymer molecule, or may comprise polymer molecules having the structure of the formula (4-2):

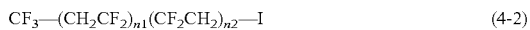

$$CF_3\text{—}(CH_2CF_2)_{n1}(CF_2CH_2)_{n2}\text{—}I \qquad (4\text{-}2)$$

in which a part of the vinylidene fluoride units face toward the opposite directions in one polymer molecule, wherein n1+n2=n=1 to 20.

Particularly preferred is the polymer consisting of polymer molecules of the formula (4-1) in which the vinylidene fluoride units face toward the same direction.

Even in the case of a mixture of polymer molecules of the formulae (4-1) and (4-2), the lower the n2 ratio (called abnormal bonding ratio (ratio of head to head and tail to tail additions)), the more preferable. For example, preferred is a mixture having an abnormal bonding ratio: (n2/(n+n1+n2))×100 of not more than 20%, further not more than 10%, particularly not more than 5%, which is calculated by NMR analysis.

The second of the novel vinylidene fluoride homopolymers of the present invention is the vinylidene fluoride homopolymer represented by the formula (5):

$$\text{I-}(A^2)CF_2CF_2)_m\text{-}(A^3)\text{-I} \tag{5}$$

wherein m is an integer of 1 to 5; $A^2$ and $A^3$ are the same or different and each is a structural unit of vinylidene fluoride homopolymer comprising crystal form I alone or as main component and the sum of number average degree of polymerization of the structural units $A^2$ and $A^3$ is 2 to 20. These polymers unexpectedly have a high purity of crystal form I.

The sum of number average degree of polymerization of the structural units $A^2$ and $A^3$ is selected within a range of 2 to 20, and a lower limit thereof is more preferably 4, further preferably 5, and an upper limit thereof is preferably 15, further preferably 12.

Namely, if the number average degree of polymerization is too low, crystals are difficult to be formed at room temperature, and if the number average degree of polymerization is too high, a purity of crystal form I is decreased (for example, a ratio of crystal form II is increased).

In the polymer of the formula (5), m can be selected from an integer of 1 to 5 and is more preferably 2, in which a purity of form I is particularly high.

The polymer of the formula (5) can be synthesized by various processes, for example, by the above-mentioned process by using a chain transfer agent of the formula (5-1):

$$\text{I}—(CF_2CF_2)_m—\text{I} \tag{5-1}$$

wherein m is an integer of 1 to 5. The use of this chain transfer agent is preferred because a polymer having a narrow molecular weight distribution can be synthesized, thereby enabling the purity of crystal form I to be increased.

In the polymer of the formula (5), a molecular weight distribution of the structural units $A^2$ and $A^3$ varies depending on the sum of number average degree of polymerization of the structural units $A^2$ and $A^3$. For example, Mw/Mn obtained by GPC analysis is not less than 1 and not more than 3, preferably not more than 2, more preferably not more than 1.5. If the molecular weight distribution is increased, a purity of crystal form 1 tends to be decreased.

The vinylidene fluoride homopolymers of the respective formulae (4) and (5) of the present invention are preferably those containing crystal form 1 satisfying (Equation 1) and (Equation 2), further preferably those containing, at high purity, crystal form satisfying (Equation 3) and (Equation 4), thereby enabling ferroelectric characteristics to be imparted effectively to the thin film of the present invention.

The end group of the vinylidene fluoride homopolymer directly obtained in the step (i) of the present invention is iodine atom or bromine atom. Also there can be used, in the method of forming a thin film of the present invention, end-modified vinylidene fluoride homopolymers obtained by modifying this end group to H or F (n=0) or an alkyl group (n=1 to 4) which may have fluorine atom, which is represented by the formula (6)

$$—C_nX^6{}_{2n+1} \tag{6}$$

wherein n is 0 or an integer of 1 to 4; $X^6$ is H or F.

When modifying the iodine atom or bromine atom to the end group of the formula (6), the iodine atom or bromine atom may be modified directly to H, F or an alkyl group or may be once modified to other functional group and then modified to the end group of the formula (6).

In the end group of the formula (6), it is particularly preferable that n is zero, namely the end group is H or F because ferroelectricity is increased when n is smaller.

In the method of forming a thin film of the first invention, the step (ii) for forming a thin film on a substrate is carried out by using the vinylidene fluoride homopolymer comprising crystal form I alone or as main component which is obtained in the mentioned step (i).

The green powder product of vinylidene fluoride homopolymer prepared in the step (i) may be applied directly on a substrate, or the vinylidene fluoride homopolymer which comprises crystal form I alone or as main component and is obtained by subjecting the green powder product of vinylidene fluoride homopolymer prepared in the step (i) to any treatments within a range not having adverse effect on crystal form I may be applied on a substrate.

Examples of steps for such treatments are, for instance, a washing step which is carried out just after the step (i) for removing low molecular weight impurities in the green polymer powder, a step for separating the vinylidene fluoride homopolymers comprising crystal form I alone or as main component and having a specific molecular weight, steps for re-precipitation and re-crystallization, a heating step for drying, a vacuum treatment step, a heat-treatment step for crystal growth and the like.

Among those steps, by separating the homopolymers having a specific molecular weight by the separation step, a purity of I-form crystal is increased, thereby enabling ferroelectric characteristics to be imparted more effectively to the thin film of the present invention. The separation step can be carried out preferably, for example, by re-precipitation method, distillation method, chromatography method, vapor deposition method or the like method.

According to the re-precipitation method, vinylidene fluoride homopolymers having the same molecular weight can be separated by allowing the green powder product of vinylidene fluoride homopolymer to be dissolved in as small an amount as possible of solvent (good solvent) and then pouring into a solvent (poor solvent), in which the green powder product of vinylidene fluoride homopolymer is low in solubility, for re-precipitation of the vinylidene fluoride homopolymer.

In this case, it is preferable that the green powder product of vinylidene fluoride homopolymer is dissolved in an amount of 1 to 80% by weight, preferably 1 to 70% by weight, more preferably 1 to 50% by weight to the good solvent. Also it is preferable that the amount of poor solvent is about 10 to about 20 times the amount of good solvent. A re-precipitation temperature is usually −30° C. to 150° C., preferably 0° C. to 80° C., more preferably 25° C. to 50° C.

The above-mentioned good solvent and poor solvent may be optionally selected depending on solubility of vinylidene fluoride homopolymer to be re-precipitated. There can be used preferably, for example, ketone solvents such as acetone, methyl ethyl ketone, methyl isobutyl ketone, cyclohexanone and acetyl acetone; ester solvents such as ethyl acetate, cellosolve acetate, n-butyl acetate, isobutyl acetate, methyl cellosove acetate, carbitol acetate and dibutyl phthalate; aldehyde solvents such as benzaldehyde; amine solvents such as dimethylamine, dibutylamine, dimethylaniline, methylamine and benzylamine; amide solvents such as N,N-dimethylformamide, N,N-dimethylacetamide and N-methyl-2-pyrrolidone; carboxylic acid anhydride solvents such as acetic anhydride; carboxylic acid solvents such as acetic acid; halogen solvents such as chloroform, dichloromethane, 1,2-dichloroethane, chlorobenzene, benzyl chloride and 1,1,2,2-tetrachloroethane; ether solvents such as tetrahydrofuran and dioxane; sulfone amide solvents such as dimethyl sulfoxide; aliphatic hydrocarbon solvents such as hexane, heptane, octane and petroleum ether; alcohol solvents such as methanol, ethanol and 1-propanol; aromatic hydrocarbon solvents such as benzene, toluene, xylene and styrene; and solvent mixtures of two or more thereof.

According to the distillation method, vinylidene fluoride homopolymers having the same molecular weight can be efficiently separated by distilling the green powder product of vinylidene fluoride homopolymer under a specific pressure (reduced pressure) and a specific temperature.

A distilling pressure is usually 0.1 Pa to 101 KPa, preferably 1 Pa to 50 KPa, more preferably 100 Pa to 1 KPa. A distilling temperature is usually 0° C. to 500° C., preferably 0° C. to 250° C., more preferably 25° C. to 200° C.

According to the washing method, vinylidene fluoride homopolymers having the same molecular weight can be separated by subjecting the green powder product of vinylidene fluoride homopolymer to washing with a solvent.

The solvent used for the washing may be optionally selected from those being capable of dissolving vinylidene fluoride homopolymer. Concretely the same solvents as exemplified in the re-precipitation method can be used.

A solvent temperature at washing is usually −30° C. to 150° C., preferably 0° C. to 80° C., more preferably 25° C. to 50° C.

The number of washing steps varies depending on kind of solvent for the washing. In principle, the washing may be carried out optional times, usually not more than 100 times, preferably not more than 50 times, more preferably not more than 10 times.

According to the chromatography method, vinylidene fluoride homopolymers having the same molecular weight can be separated efficiently.

When the mobile phase is one dissolving vinylidene fluoride homopolymer, any of known methods may be employed. For example, liquid phase chromatography and gas chromatography are used preferably. A temperature in the chromatography method is usually −30° C. to 150° C., preferably 0° C. to 100° C., more preferably 25° C. to 80° C.

According to the vapor deposition method, vinylidene fluoride homopolymers having the same molecular weight can be efficiently separated by vapor deposition of the green powder product of vinylidene fluoride homopolymer under a specific pressure (reduced pressure) and a specific temperature.

In the vapor deposition, the green powder product of vinylidene fluoride homopolymer is subjected to heating or cooling, and a vapor deposition temperature is usually −30° C. to 1,000° C., preferably 0° C. to 800° C., more preferably 0° C. to 500° C. A vapor deposition pressure in a system is usually $1 \times 10^{-6}$ Pa to 100 KPa, preferably not more than 1 KPa, more preferably not more than 1 Pa.

It is preferable to employ the distillation method or chromatography method because vinylidene fluoride homopolymers of the same molecular weight can be separated easily efficiently.

As the molecular weight distribution is made narrower by such separation steps, a purity of crystal form I is increased and ferroelectric characteristics can be imparted effectively to the thin film of the present invention. Therefore it is preferable to increase the purity of vinylidene fluoride homopolymers having the same molecular weight to not less than 70% by weight, further not less than 80% by weight, further preferably not less than 90% by weight, particularly not less than 95% by weight.

Also the step (ii) for forming a thin film may be carried out after a step of blending a solvent and additives to the vinylidene fluoride homopolymer comprising crystal form I alone or as main component and forming into a coating.

In the step (ii) of the present invention, there can be used various methods of forming a thin film. There can be preferably used, for example, a method (coating solution method) of dissolving or dispersing vinylidene fluoride homopolymer in a liquid medium and applying in the form of a coating solution (coating composition); a method (powder coating method) of applying vinylidene fluoride homopolymer in the form of powder directly on a substrate; a method (vacuum vapor deposition method) of subjecting vinylidene fluoride homopolymer powder to sublimation in vacuo and/or under heating and then coating by vapor deposition, and the like method.

In the method of applying the vinylidene fluoride homopolymer in the form of a coating solution (coating composition), there can be used a liquid medium which can dissolve or uniformly disperse the vinylidene fluoride homopolymer. In order to control a thickness of the thin film, particularly preferred is a liquid medium which can dissolve the vinylidene fluoride homopolymer.

Preferred examples of the liquid medium are, for instance, ketone solvents such as acetone, methyl ethyl ketone, methyl isobutyl ketone, cyclohexanone and acetyl acetone; ester solvents such as ethyl acetate, cellosolve acetate, n-butyl acetate, isobutyl acetate, methyl cellosolve acetate, carbitol acetate and dibutylphthalate; aldehyde solvents such as benzaldehyde; amine solvents such as dimethylamine, dibutylamine, dimethylaniline, methylamine and benzylamine; amide solvents such as N,N-dimethylformamide, N,N-dimethylacetamide and N-methyl-2-pyrrolidone; carboxylic acid anhydride solvents such as acetic anhydride; carboxylic acid solvents such as acetic acid; halogen solvents such as chloroform, dichloromethane, 1,2-dichloroethane and 1,1,2,2-tetrachloroethane; ether solvents such as tetrahydrofuran and dioxane; sulfone amide solvents such as dimethyl sulfoxide; and the like.

Particularly preferred are ketone solvents and amide solvents because vinylidene fluoride homopolymer is dissolved therein satisfactorily.

Also when vinylidene fluoride homopolymer is uniformly dispersed stably in the form of fine particles in a medium, a thin film can be formed even in the case of the homopolymer being insoluble in a liquid solvent. For example, an aqueous dispersion of vinylidene fluoride homopolymer can be used.

A concentration of vinylidene fluoride homopolymer in the coating solution varies depending on an intended coating thickness, a viscosity of the coating solution, etc. The concentration is not less than 0.1% by weight, preferably not less than 0.5% by weight, more preferably not less than 1% by weight, and not more than 50% by weight, preferably not more than 30% by weight, more preferably not more than 20% by weight.

For applying those coating solutions on a substrate, there can be used known coating methods such as spin coating, dip coating, spray coating, roll coating and gravure coating. For efficiently forming a thin film, the spin coating method and gravure coating method are preferred, and particularly the spin coating method is preferred.

After the application by the above-mentioned method, a drying step may be carried out for removing the solvent. For the drying, for example, air drying at room temperature, drying by heating, vacuum drying and the like can be used. In the drying, attention should be paid not to dry excessively at high temperature since there is a case where the crystal form I is changed.

Accordingly, it is preferable to dry by heating at a temperature lower than a melting point of vinylidene fluoride homopolymer. The temperature for drying by heating varies depending on a boiling point of a solvent to be used, and is not less than 30° C., preferably not less than 40° C., more preferably not less than 50° C. and not more than 100° C., preferably not more than 80° C., more preferably not more than 70° C.

The thus formed thin film of vinylidene fluoride homopolymer on a substrate by application in the form of a coating solution maintains crystal form I and has an ability of exhibiting excellent ferroelectricity.

Also preferred is a method of forming a thin film on a substrate by the vacuum vapor deposition method by using a vacuum vapor deposition equipment.

A vacuum vapor deposition temperature and vacuum degree are optionally selected depending on a degree of polymerization and sublimation property of vinylidene fluoride homopolymer. The vapor deposition temperature is from room temperature to 200° C., preferably not more than 100° C. The substrate temperature is from 0° C. to 100° C., preferably not less than room temperature and not more than 50° C. The vacuum degree is not more than $10^{-2}$ Pa, preferably not more than $10^{-4}$ Pa.

In this vacuum vapor deposition method, by use of the method of forming a thin film of the present invention including the step (i), a thin film of vinylidene fluoride homopolymer having crystal form I can be formed easily under normal conditions such as mom temperature even without setting the substrate particularly at very low temperature.

In the method of forming a thin film of the present invention, kind of a substrate is not limited, and a thin film of vinylidene fluoride homopolymer having crystal form I can be formed on various kinds of substrates.

Kind of a substrate is optionally selected depending on an intended object and application of the laminated article, and is selected from silicon substrates, metallic substrates, glass substrates, ceramic substrates, resin substrates and the like.

For utilizing electrical properties of the thin film of vinylidene fluoride homopolymer having crystal form I of the present invention, preferred are electrically conductive substrates being capable of forming an electrode. Also insulating substrates such as silicon substrates, glass substrates, ceramic substrates and resin substrates on which a thin film of electrically conductive material is formed are preferred as the electrically conductive substrates.

As an electrically conductive substrate or a metallic material for thin film, there can be used aluminum, copper, chromium, nickel, zinc, stainless steel, gold, silver, platinum, tantalum, titanium, niobium, molybdenum, indium tin oxide (ITO) and the like. Particularly preferred are silicon wafers on which a thin film of aluminum, gold, silver, platinum, tantalum, titanium or the like is formed. As the metallic substrate, aluminum, copper, gold, silver and platinum are also preferred.

Those electrically conductive thin films provided on a substrate surface may be previously subjected to patterning of intended circuit by a known method such as photolithography, mask deposition or the like, as case demands.

Also a substrate which is coated with a polymer on its surface may be used.

On those substrates are formed thin films of vinylidene fluoride homopolymer having crystal form I by the mentioned method (step (ii)).

A thickness of thin film of vinylidene fluoride homopolymer having crystal form I is optionally selected depending on an intended object and application of the laminated article. The thickness is usually not less than 1 nm, preferably not less than 5 nm, particularly preferably not less than 10 nm, and not more than 10 μm, preferably not more than 1 μm, particularly preferably not more than 500 nm.

In the method of forming a thin film of the present invention, after forming the thin film of vinylidene fluoride homopolymer on a substrate, a step for heat treating (heat treating step (iii)) may be further carried out for the purpose of enhancing ferroelectric characteristics of the formed thin film of vinylidene fluoride homopolymer. The heat treating step (iii) of the thin film of vinylidene fluoride homopolymer is usually carried out for the purpose of growth of crystals in the thin film of vinylidene fluoride homopolymer to increase the crystal size, and as a result, ferroelectric characteristics can be enhanced.

A heat treating temperature in the heat treating step (iii) is optionally selected depending on a number average degree of polymerization and crystalline melting point of the vinylidene fluoride homopolymer and kind of a substrate, and is usually not less than 50° C., preferably not less than 60° C., more preferably not less than 70° C., particularly preferably not less than 80° C., and an upper limit thereof is usually a temperature lower than a crystalline melting point of the vinylidene fluoride homopolymer, preferably a temperature lower than the crystalline melting point by 5° C., more preferably a temperature lower than the crystalline melting point by 10° C.

A heat treating time is usually not less than about 10 minutes, preferably not less than 20 minutes, more preferably not less than 30 minutes, and not more than about 10 hours, preferably not more than 5 hours, more preferably not more than 3 hours, particularly preferably not more than about 2 hours. It is preferable that after the heating, the film is allowed to stand at room temperature for air cooling slowly.

It is preferable to use the preferred vinylidene fluoride homopolymer of the present invention comprising crystal form 1 alone or as main component because enough ferroelectric characteristics can be exhibited even without carrying out the above-mentioned heat treating step (iii).

In the method of forming a thin film of the present invention, after forming the thin film, the polarization step (iv) may be further carried out after carrying out the above-mentioned heat-treating step (iii) or without carrying out the step (iii). The polarization step (iv) is carried out for the purpose of making the thin film of the present invention surely exhibit ferroelectricity.

For the polarization, known methods can be used similarly. For example, there can be used a method of carrying out vapor deposition of an electrode on the film or contacting an electrode to the film and then applying electric field of direct or alternating current or direct or alternating voltage on the electrode, a method of corona discharging or the like method.

The applied electric field in the polarization step (iv) can be optionally selected depending on the thickness of the thin film, a proportion of crystal form I, etc., and is usually not less than 10 MV/m, preferably not less than 50 MV/m, more preferably not less than 80 MV/m, and not more than dielectric breakdown electric voltage, preferably not more than 250 MV/m, more preferably not more than 200 MV/m. If the applied electric field is too low or the applying time is too short, enough polarization is not attained. Also too high applied electric field or too long applying time is not preferred because bonding of polymer molecules is cleaved even partially.

The applying time is usually not less than 20 nanoseconds, preferably not less than 1 second, more preferably not less than 1 minute, and up to about 48 hours, preferably six hours, more preferably two hours.

A thin film temperature in the polarization step (iv) is usually not less than 0° C., preferably not less than 10° C., more preferably not less than 25° C., and not more than a crystalline melting point of vinylidene fluoride homopolymer, preferably not more than 120° C., more preferably not more than 85° C.

Also the heat-treating step (iii) and the polarization step (iv) may be carried out at the same time, thereby enabling higher ferroelectric characteristics to be exhibited.

Further the thin film of vinylidene fluoride homopolymer in the thus obtained laminated article may be subjected to patterning of intended circuit by a known method such as photolithography, mask deposition or the like, as case demands.

Also as case demands, a layer of other material may be provided on the thin film of vinylidene fluoride homopolymer in the thus obtained laminated article.

For example, it is possible to make multiple layers by providing the thin film of vinylidene fluoride homopolymer between electrically conductive material layers being capable of becoming the same electrode as mentioned above or insulating layers of silicon, ceramic, resin or the like in the form of sandwich.

The thus obtained laminated article has ferroelectricity.

In the present invention, ferroelectricity is a property that permanent dipoles inside a substance are oriented in the same direction by action of any force and the substance has polarization even when an electric field is not applied (polarization generated even without an electric field is called spontaneous polarization). Also ferroelectricity is a property that the spontaneous polarization can be inverted by an outside electric field. Whether or not a substance has ferroelectricity is known by the fact that when examining a relation between the electric field E and the electric displacement density ID, if the substance is a ferroelectric substance, a hysteresis curve like that of a ferromagnetic substance is shown when an alternating electric field having a large amplitude to a certain extent is applied thereto.

According to the method of the present invention, for example, with respect to a laminated article comprising a layer of vinylidene fluoride homopolymer and electrodes of Al thin films provided on both sides thereof, when a triangular wave voltage having a frequency of 15 mHz and an amplitude of 120 V is applied between both electrodes, not only a rectangular hysteresis curve can be obtained but also a value of remanence polarization calculated therefrom can be not less than 75 $mC/m^2$, preferably not less than 90 $mC/m^2$, more preferably not less than 110 $mC/m^2$, particularly preferably not less than 120 $mC/m^2$, especially not less than 135 $mC/m^2$.

A substance having ferroelectricity also has properties corresponding to electric or optical functions such as piezo electric property, pyroelectric property, electro-optical effect and non-linear optical effect.

Because of those properties, the thin film and laminated article obtained in the present invention are applicable to devices using piezo electric property, pyroelectric property, electro-optical effect and non-linear optical effect such as FE-RAM, infrared sensor, microphone, speaker, poster with voice, head phone, electronic musical instruments, artificial tactile organ, pulsimeter, hearing aid, hemadynamometer, phonocardiograph, ultrasonic diagnostic device, ultrasonic microscope, ultrasonic hyperthermia equipment, thermograph, micro-earthquake seismometer, landslide preperception meter, proximity warning (distance meter) intruder detector, keyboard switch, bimorph display for underwater communication, sonar, optical shutter, optical fiber voltmeter, hydrophone, ultrasonic optical modulation and polarization device, acoustic delay line, ultrasonic camera, POSFET, accelerometer, tool mulfunction sensor, AE detector, sensor for robot, impact sensor, flow meter, vibration meter, ultrasonic flaw detector, ultrasonic thickness meter, fire alarm, intruder detection, piezo-electric vidicon, copying machine, touch panel, endothermic and exothermic reaction detector, optical intensity modulator, optical phase modulator and optical circuit switching element.

EXAMPLE

The present invention is then explained by means of examples and preparation examples, but is not limited to such examples.

First, methods of measuring parameters used in the present invention are explained below.

[1] Method of Measuring a Degree of Polymerization of Vinylidene fluoride (VdF) polymer (1) Degree of polymerization (n) of $CF_3(VdF)_nI$ Measured by $^{19}$F-NMR. Concretely calculated by the following equation using a peak area (derived from $CF_3$—) around −61 ppm and a peak area (derived from —$CF_2$—$CH_2$—) around −90 to −96 ppm.

(Degree of polymerization)=((Peak area around −90 to −96 ppm)/2)/((Peak area around −61 ppm)/3)

(2) Degree of polymerization (n) of $CF_3CF_2(VdF)_nI$

Measured by $^{19}$F-NMR. Concretely calculated by the following equation using a peak area (derived from $CF_3$—) around −86 ppm and a peak area (derived from —$CF_2$—$CH_2$—) around −90 to −96 ppm.

(Degree of polymerization)=((Peak area around −90 to −96 ppm)/2)/((Peak area around −86 ppm)/3)

(3) Degree of polymerization (n+m) of $I(VdF)_nCF_2CF_2CF_2CF_2(VdF)_mI$

Measured by $^{19}$F-NMR. Concretely calculated by the following equation using the sum of a peak area around −112 ppm and a peak area around −124 ppm (both derived from —$CF_2CF_2CF_2CF_2$—) and a peak area (derived from —$CF_2$—$CH_2$—) around −90 to −96 ppm.

(Degree of polymerization)=((Peak area around −90 to −96 ppm)/2)/((Sum of peak area around −112 ppm and peak area around −124 ppm)/8)

[2] Measuring (Analysis) Methods and Equipment (1) IR analysis (1-1) Measuring conditions KBr method is employed. After 1 to 5 mg of vinylidene fluoride polymer powder is mixed to 100 to 500 mg of KBr powder and pressure is applied for pelletizing, the obtained pellets are fixed to a measuring equipment and measurement is carried out at 25° C.

(1-2) Measuring equipment

FT-IR spectrometer 1760x available from Perkin Elmer Co., Ltd.

(2) $^1$H-NMR and $^{19}$F-NMR analyses (2-1) Measuring conditions

Measurement is carried out by dissolving 10 to 20 mg of vinylidene fluoride polymer powder in do-acetone and setting the obtained sample on a probe.

(2-2) Measuring equipment
    AC-300P available from Brucker
  (3) Powder X-ray diffraction analysis
  (3-1) Measuring conditions
    Measurement is carried out by applying vinylidene fluoride polymer powder on a glass plate for specific use for this analysis and setting the glass plate on measuring equipment.
  (3-2) Measuring equipment
    Rotaflex available from Rigaku Co.
  (4) Confirmation of ferroelectricity (D-E hysteresis curve)
    When a material has ferroelectricity, a D-E hysteresis curve of the material shows a rectangular shape. In the present invention, electric current and voltage characteristics are examined under the following conditions and a D-E hysteresis curve is drawn to judge whether or not ferroelectricity is present.
  (4-1) Measuring conditions
    A triangular wave voltage having a frequency of 15 mHz and an amplitude of 120 V is applied on aluminum electrodes formed on both sides of VdF thin film.
  (4-2) Measuring equipment
    Electric characteristics evaluation equipment for dielectric thin film available from Agilent Technologies
  (5) Molecular weight distribution analysis
  (5-1) Measuring conditions
    Measurement is carried out at 35° C. by dissolving vinylidene fluoride polymer in THF in an amount of 0.1 to 0.2% by weight and setting on measuring equipment.
  (5-2) Measuring equipment
    HLC-8020 (equipment) available from Toso Kabushiki Kaisha and Shodex GPC-KF-801, GPC-KF-802 and two GPC-KF-806MX2 (columns) are used.
  (6) Measurement of abnormal bonding ratio Abnormal bonding ratio (%)=(n2/(n+n1+n2))×100

The abnormal bonding ratio is obtained by $^{19}$F-NMR analysis, and is concretely calculated by the above equation from the sum of a peak area around −112 ppm and a peak area around −124 ppm (both derived from abnormal bonding) (=n2) and a peak area (derived from —CF$_2$—CH$_2$—) around −90 to −96 ppm (=n+n1).

(Degree of polymerization)=(Sum of peak area around
  −112 ppm and peak area around −124 ppm)/
  ((Sum of peak area around −112 ppm and peak
  area around −124 ppm)+(Peak area around −90
  to −96 ppm))

(Peak area around −90 to −96 ppm) is n1, and (Sum of peak area around −112 ppm and peak area around −124 ppm) is n2.

Preparation Example 1

Synthesis of CF$_3$(VdF)$_n$I (1-1) Synthesis of CF$_3$(VdF)$_{8.1}$I (n=8.1)
    Into a 300 ml stainless steel autoclave equipped with a valve, pressure gauge and thermometer was poured 50 g of HCFC-225, and while cooling with a dry ice/methanol solution, 0.78 g of di-n-propylperoxy dicarbonate (50% by weight of methanol solution) was added and the inside of a system was sufficiently replaced with nitrogen gas. After the inside pressure of the system was reduced, 5.2 g of CF$_3$I was introduced through the valve, and after heating of the system up to 45° C., VdF was introduced until the inside pressure of the system became 0.8 MPaG. While maintaining the inside pressure and temperature of the system at 0.8 MPaG and 45° C., respectively, VdF was continuously introduced and 9-hour reaction was carried out.

After completion of the reaction, the inside temperature of the system was decreased to 25° C. and the unreacted substances (VdF and CF$_3$I) were released. Then the precipitated solid reaction product (hereinafter referred to as "VdF polymer") was taken out and subjected to vacuum drying in a desiccator until a constant weight was reached to obtain 13.2 g of VdF polymer.

With respect to this VdF polymer, a degree (n) of polymerization obtained by $^{19}$F-NMR analysis was 8.1. An abnormal bonding ratio was 4.0%, and Mw/Mn was 1.06.

Figure 6:
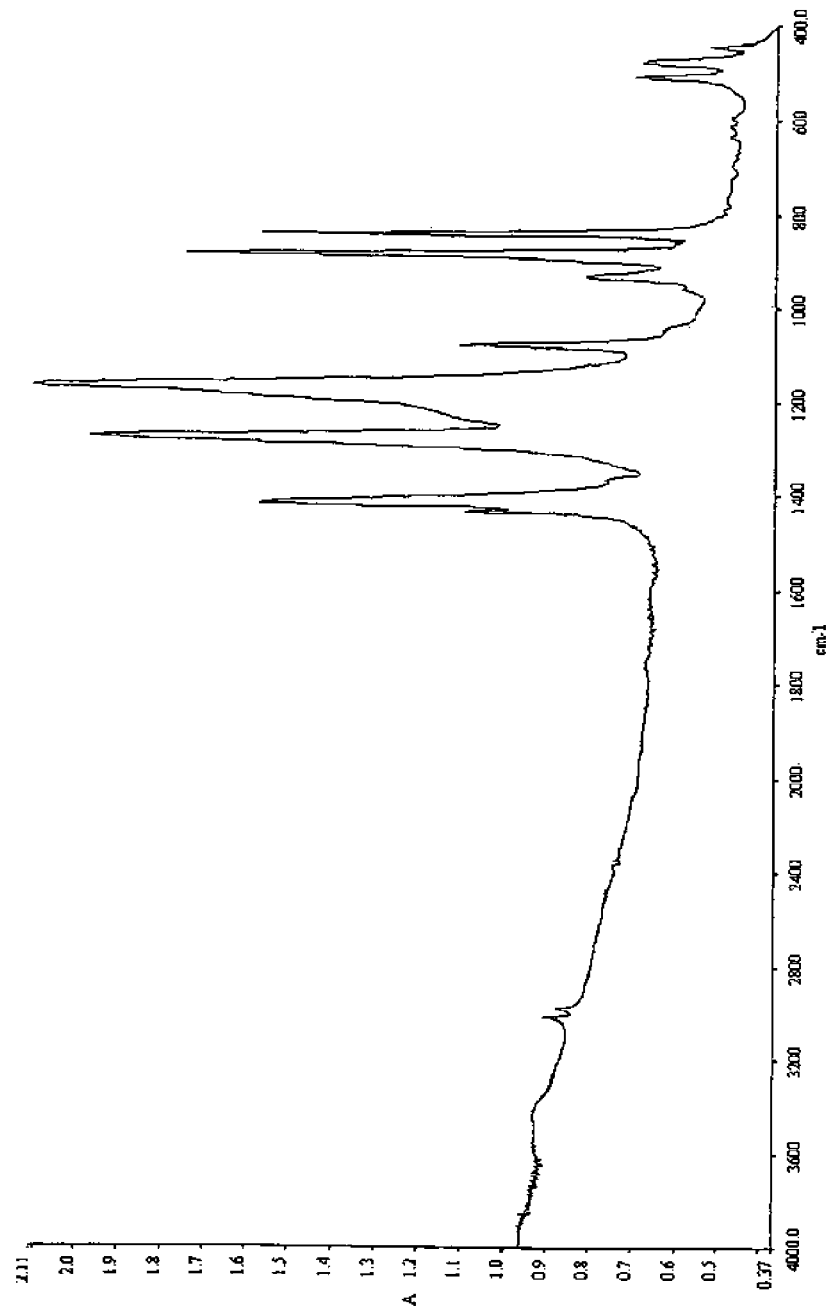
FIG. 6 is an IR chart of vinylidene fluoride homopolymer of all-I-form crystal structure which is obtained in (1-1) of Preparation Example 1.

With respect to this VdF polymer, IR analysis and powder X-ray diffraction analysis were carried out. As a result, only a peak which was characteristic to crystal form I was recognized and it was confirmed that the VdF polymer was one having all-I-form crystal structure (cf. FIG. 6).

(1-2) Synthesis of CF$_3$(VdF)$_{5.2}$I (n=5.2)
    Into a 300 ml stainless steel autoclave equipped with a valve, pressure gauge and thermometer was poured 50 g of HCFC-225, and while cooling with a dry ice/methanol solution, 0.53 g of di-n-propylperoxy dicarbonate (50% by weight of methanol solution) was added and the inside of a system was sufficiently replaced with nitrogen gas. After the inside pressure of the system was reduced, 5.4 g of CF$_3$I was introduced through the valve, and after heating of the system up to 45° C., VdF was introduced until the inside pressure of the system became 0.8 MPaG. While maintaining the inside pressure and temperature of the system at 0.8 MPaG and 45° C., respectively, VdF was continuously introduced and 7.5-hour reaction was carried out.

After completion of the reaction, the inside temperature of the system was decreased to 25° C. and the unreacted substances (VdF and CF$_3$I) were released. Then the precipitated solid reaction product (VdF polymer) was taken out and subjected to vacuum drying in a desiccator until a constant weight was reached to obtain 10.0 g of VdF polymer.

With respect to this VdF polymer, a degree (n) of polymerization obtained by $^{19}$F-NMR analysis was 5.2. An abnormal bonding ratio was 4.3%, and Mw/Mn was 1.08.

With respect to this VdF polymer, IR analysis and powder X-ray diffraction analysis were carried out. As a result, only a peak which was characteristic to crystal form I was recognized and it was confirmed that the VdF polymer was one having all-I-form crystal structure.

(1-3) Synthesis of CF$_3$(VdF)$_{10.1}$I (n=10.1)
    Into a 300 ml stainless steel autoclave equipped with a valve, pressure gauge and thermometer was poured 50 g of HCFC-225, and while cooling with a dry ice/methanol solution, 0.53 g of di-n-propylperoxy dicarbonate (50% by weight of methanol solution) was added and the inside of a system was sufficiently replaced with nitrogen gas. After the inside pressure of the system was reduced, 5.2 g of CF$_3$I was introduced through the valve, and after heating of the system up to 45° C., VdF was introduced until the inside pressure of the system became 0.8 MPaG. While maintaining the inside pressure and temperature of the system at 0.8 MPaG and 45° C., respectively, VdF was continuously introduced and 12-hour reaction was carried out.

After completion of the reaction, the inside temperature of the system was decreased to 25° C. and the unreacted substances (VdF and CF$_3$I) were released. Then the precipitated solid reaction product (VdF polymer) was taken out and subjected to vacuum drying in a desiccator until a constant weight was reached to obtain 13.4 g of VdF polymer.

With respect to this VdF polymer, a degree (n) of polymerization obtained by $^{19}$F-NMR analysis was 10.1. An abnormal bonding ratio was 3.9%, and Mw/Mn was 1.08.

With respect to this VdF polymer, IR analysis and powder X-ray diffraction analysis were carried out. As a result, only a peak which was characteristic to crystal form I was recognized and it was confirmed that the VdF polymer was one having all-I-form crystal structure.

(1-4) Synthesis of $CF_3(VdF)_{11.0}I$ (n=11.0)

Into a 300 ml stainless steel autoclave equipped with a valve, pressure gauge and thermometer was poured 50 g of HCFC-225, and while cooling with a dry ice/methanol solution, 0.38 g of di-n-propylperoxy dicarbonate (50% by weight of methanol solution) was added and the inside of a system was sufficiently replaced with nitrogen gas. After the inside pressure of the system was reduced, 3.5 g of $CF_3I$ was introduced through the valve, and after heating of the system up to 45° C., VdF was introduced until the inside pressure of the system became 0.8 MPaG. While maintaining the inside pressure and temperature of the system at 0.8 MPaG and 45° C., respectively, VdF was continuously introduced and 9-hour reaction was carried out.

After completion of the reaction, the inside temperature of the system was decreased to 25° C. and the unreacted substances (VdF and $CF_3I$) were released. Then the precipitated solid reaction product (VdF polymer) was taken out and subjected to vacuum drying in a desiccator until a constant weight was reached to obtain 11.2 g of VdF polymer.

With respect to this VdF polymer, a degree (n) of polymerization obtained by $^{19}F$-NMR analysis was 11.0. An abnormal bonding ratio was 4.4%, and Mw/Mn was 1.13.

With respect to this VdF polymer, IR analysis was carried out. As a result, both of peaks which were characteristic to crystal forms I and H were recognized and it was confirmed that crystal form I and crystal form II were mixed. Further the calculated content (F(I)) of crystal form I was 85% by weight.

(1-5) Synthesis of $CF_3(VdF)_{18.4}I$ (n=18.4)

Into a 300 ml stainless steel autoclave equipped with a valve, pressure gauge and thermometer was poured 50 g of HCFC-225, and while cooling with a dry ice/methanol solution, 0.16 g of di-n-propylperoxy dicarbonate (50% by weight of methanol solution) was added and the inside of a system was sufficiently replaced with nitrogen gas. After the inside pressure of the system was reduced, 1.5 g of $CF_3I$ was introduced through the valve, and after heating of the system up to 45° C., VdF was introduced until the inside pressure of the system became 0.8 MPaG. While maintaining the inside pressure and temperature of the system at 0.8 MPaG and 45° C., respectively, VdF was continuously introduced and 9-hour reaction was carried out.

After completion of the reaction, the inside temperature of the system was decreased to 25° C. and the unreacted substances (VdF and $CF_3I$) were released. Then the precipitated solid reaction product (VdF polymer) was taken out and subjected to vacuum drying in a desiccator until a constant weight was reached to obtain 7.9 g of VdF polymer.

With respect to this VdF polymer, a degree (n) of polymerization obtained by $^{19}F$-NMR analysis was 18.4. An abnormal bonding ratio was 3.8%, and Mw/Mn was 1.17.

With respect to this VdF polymer, IR analysis was carried out. As a result, both of peaks which were characteristic to crystal forms I and II were recognized and it was confirmed that crystal forms I and II were mixed. Further the calculated content (F(I)) of crystal form I was 18% by weight.

(1-6) Synthesis of $CF_3(VdF)_{14.6}I$ (n=14.6)

Into a 300 ml stainless steel autoclave equipped with a valve, pressure gauge and thermometer was poured 50 g of HCFC-225, and while cooling with a dry ice/methanol solution, 0.27 g of di-n-propylperoxy dicarbonate (50% by weight of methanol solution) was added and the inside of a system was sufficiently replaced with nitrogen gas. After the inside pressure of the system was reduced, 2.5 g of $CF_3I$ was introduced through the valve, and after heating of the system up to 45° C., VdF was introduced until the inside pressure of the system became 0.8 MPaG. While maintaining the inside pressure and temperature of the system at 0.8 MPaG and 45° C., respectively, VdF was continuously introduced and 9-hour reaction was carried out.

After completion of the reaction, the inside temperature of the system was decreased to 25° C. and the unreacted substances (VdF and $CF_3I$) were released. Then the precipitated solid reaction product (VdF polymer) was taken out and subjected to vacuum drying in a desiccator until a constant weight was reached to obtain 12.2 g of VdF polymer.

With respect to this VdF polymer, a degree (n) of polymerization obtained by $^{19}F$-NMR analysis was 14.6. An abnormal bonding ratio was 4.1%, and Mw/Mn was 1.14.

With respect to this VdF polymer, IR analysis was carried out. As a result, both of peaks which were characteristic to crystal forms I and II were recognized and it was confirmed that crystal form I and II were mixed. Further the calculated content (F(I)) of crystal form I was 60% by weight.

(1-7) Synthesis and separation of $CF_3(VdF)_3I$ (n=3)

Into a 300 ml stainless steel autoclave equipped with a valve, pressure gauge and thermometer was poured 500 g of HCFC-225, and while cooling with a dry ice/methanol solution, 21 g of di-n-propylperoxy dicarbonate (50% by weight of methanol solution) was added and the inside of a system was sufficiently replaced with nitrogen gas. After the inside pressure of the system was reduced, 200 g of $CF_3I$ was introduced through the valve, and after heating of the system up to 45° C., VdF was introduced until the inside pressure of the system became 0.8 MPaG. While maintaining the inside pressure and temperature of the system at 0.8 MPaG and 45° C., respectively, VdF was continuously introduced and 3.5-hour reaction was carried out.

After completion of the reaction, the inside temperature of the system was decreased to 25° C. and the unreacted substances (VdF and $CF_3I$) were released. Then the precipitated solid reaction product was filtrated off and a filtrate was subjected to fractional distillation under reduced pressure (5 mmHg). The distillate of 55° C. was analyzed by $^{19}F$-NMR analysis and the degree (n) of polymerization of the distillate of 55° C. was 3. The polymer of n=3 was in the form of liquid at 25° C.

(1-8) Synthesis of mixture of crystal form I of $CF_3(VdF)_{8.1}I$ (n=8.1) and crystal form III 3 g of the VdF polymer powder having all-I-form crystal structure of $CF_3(VdF)_{8.1}I$ (n=8.1) synthesized in (1-1) above was put in a petri dish, and the dish was placed in a desiccator. The powder was heated at 200° C. for one hour and completely melted. Then the dish was taken out from the desiccator and allowed to stand at 25° C. for rapid cooling to 25° C.

Figure 7:
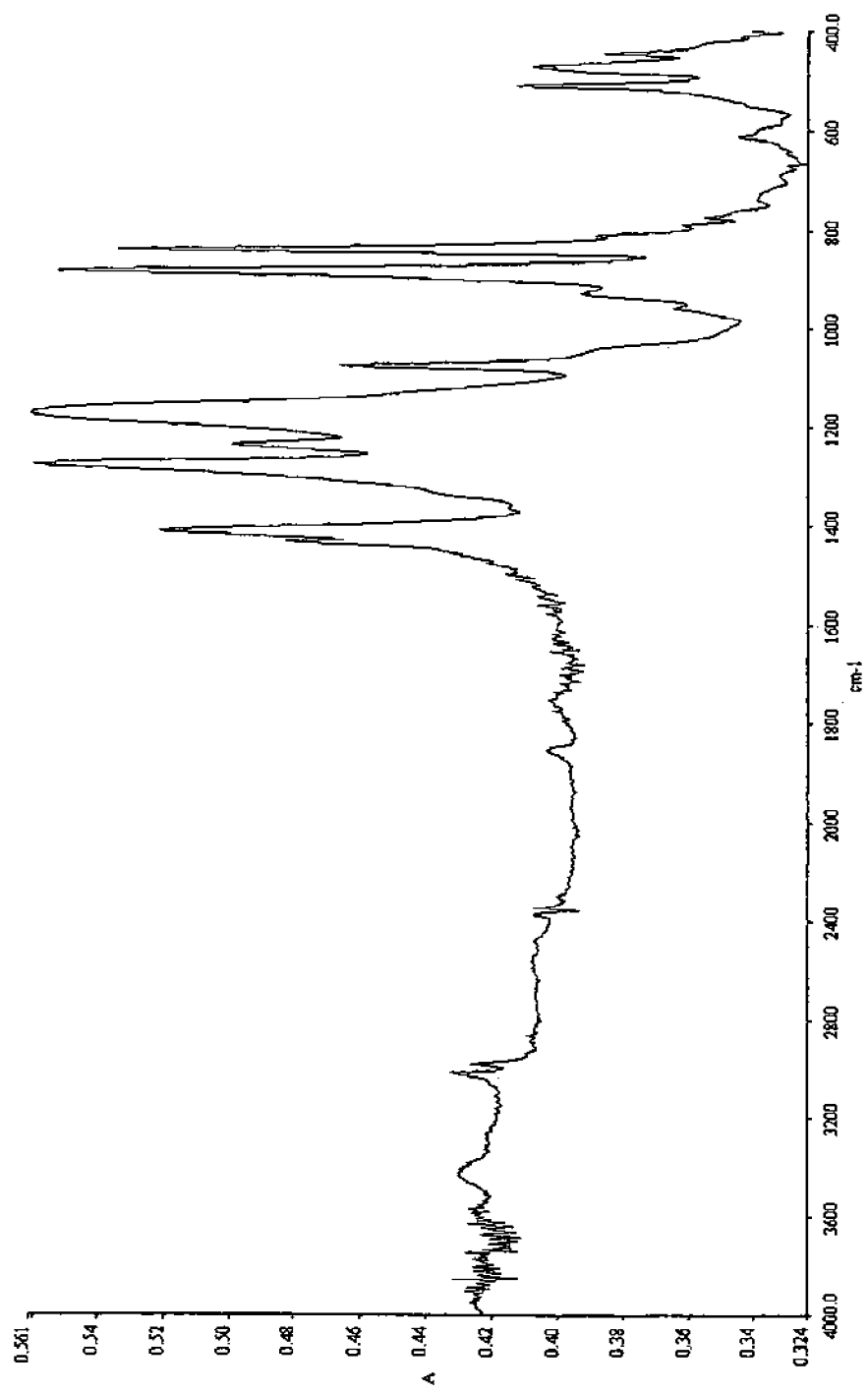
FIG. 7 is an IR chart of vinylidene fluoride homopolymer comprising a mixture of I-form and III-form crystal structures which is obtained in (1-8) of Preparation Example 1.

With respect to the obtained VdF polymer, IR analysis was carried out. As a result, both of peaks which were characteristic to crystal forms I and III were recognized and it was confirmed that crystal form I and crystal form III were mixed. Further the calculated content (F(I)) of crystal form I was 67% by weight (cf. FIG. 7).

Preparation Example 2

Synthesis of $CF_3CF_2(VdF)_nI$ (2-1) Synthesis of $CF_3CF_2(VdF)_{10.9}I$ (n=10.9)

Into a 300 ml stainless steel autoclave equipped with a valve, pressure gauge and thermometer was poured 50 g of HCFC-225, and while cooling with a dry ice/methanol solution, 0.08 g of di-n-propylperoxy dicarbonate (50% by weight of methanol solution) was added and the inside of a system was sufficiently replaced with nitrogen gas. After the inside pressure of the system was reduced, 1.96 g of $CF_3CF_2I$ was introduced through the valve, and after heating of the system up to 45° C., VdF was introduced until the inside pressure of the system became 0.8 MPaG. While maintaining the inside pressure and temperature of the system at 0.8 MPaG and 45° C., respectively, VdF was continuously introduced and 9-hour reaction was carried out.

After completion of the reaction, the inside temperature of the system was decreased to 25° C. and the unreacted substances (VdF and $CF_3CF_2I$) were released. Then the precipitated solid reaction product (VdF polymer) was taken out and subjected to vacuum drying in a desiccator until a constant weight was reached to obtain 7.3 g of VdF polymer.

With respect to this VdF polymer, a degree (n) of polymerization obtained by $^{19}$F-NMR analysis was 10.9. Also Mw/Mn was 1.10.

Figure 8:
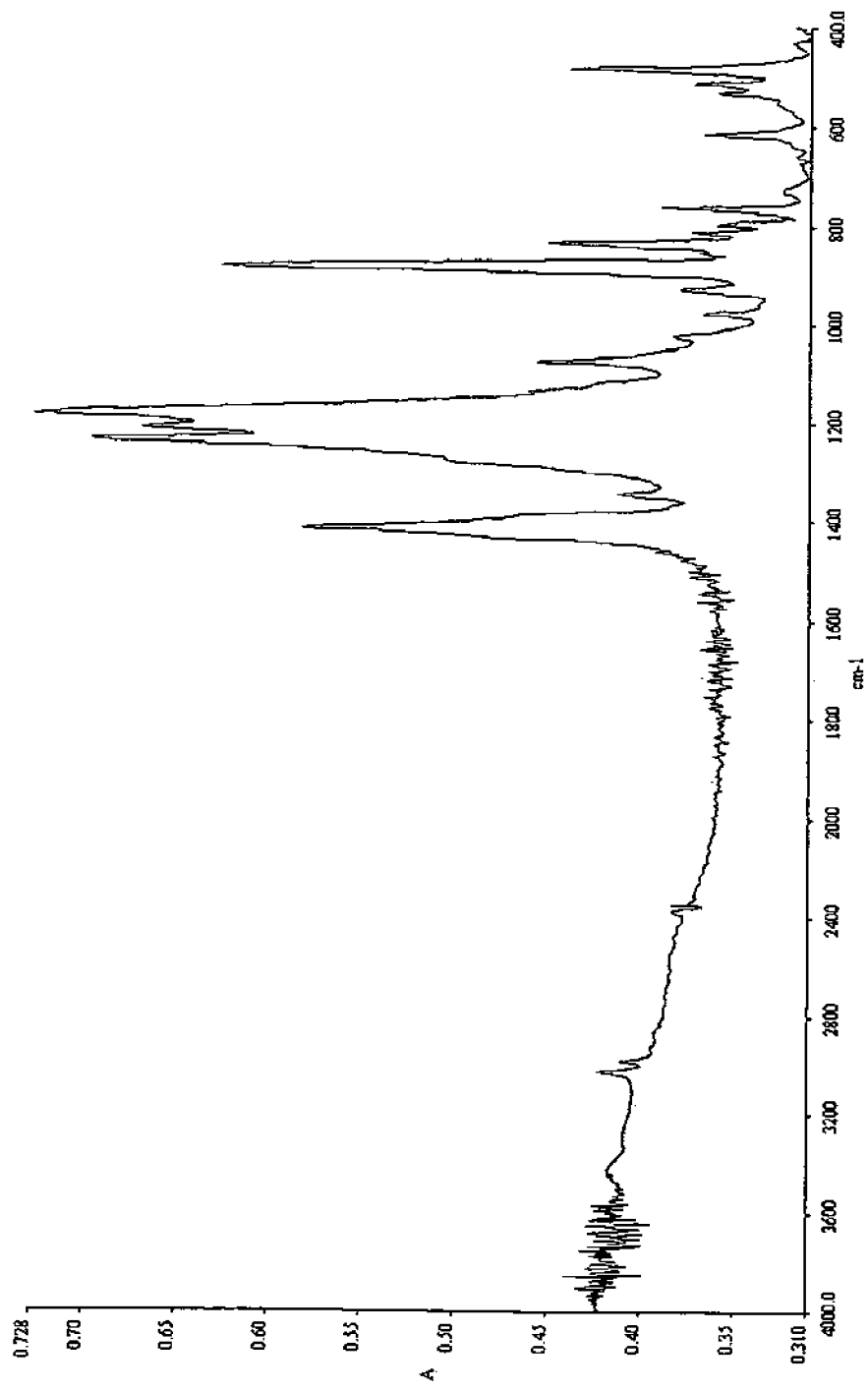
FIG. 8 is an IR chart of vinylidene fluoride homopolymer comprising a mixture of crystal forms II and III which is obtained in (2-1) of Preparation Example 2.

With respect to this VdF polymer, IR analysis was carried out. As a result, both of peaks which were characteristic to crystal forms II and III were recognized and it was confirmed that crystal form II and crystal form III were mixed. Further the calculated content (F(III)) of crystal form III was 57% by weight (cf. FIG. 8).

Preparation Example 3

Synthesis of $I(VdF)_nC_4F_8(VdF)_mI$ (3-1) Synthesis of $I(VdF)_n(CF_2CF_2)_2(VdF)_mI$ (n+m=18.7)

Into a 300 ml stainless steel autoclave equipped with a valve, pressure gauge and thermometer was poured 50 g of HCFC-225, and while cooling with a dry ice/methanol solution, 0.27 g of di-n-propylperoxy dicarbonate (50% by weight of methanol solution) was added and the inside of a system was sufficiently replaced with nitrogen gas. After the inside pressure of the system was reduced, 1.96 g of $I(CF_2CF_2)_2I$ was introduced through the valve, and after heating of the system up to 45° C., VdF was introduced until the inside pressure of the system became 0.8 MPaG. While maintaining the inside pressure and temperature of the system at 0.8 MPaG and 45° C., respectively, VdF was continuously introduced and 9-hour reaction was carried out.

After completion of the reaction, the inside temperature of the system was decreased to 25° C. and the unreacted substances (VdF and $I(CF_2CF_2)_2I$) were released. Then after the precipitated solid reaction product (VdF polymer) was taken out by filtration and washed with HCFC-225, the product was subjected to vacuum drying in a desiccator until a constant weight was reached to obtain 8.8 g of VdF polymer.

With respect to this VdF polymer, a degree (n+m) of polymerization obtained by $^{19}$F-NMR analysis was 8.7. Also Mw/Mn was 1.03.

Figure 9:
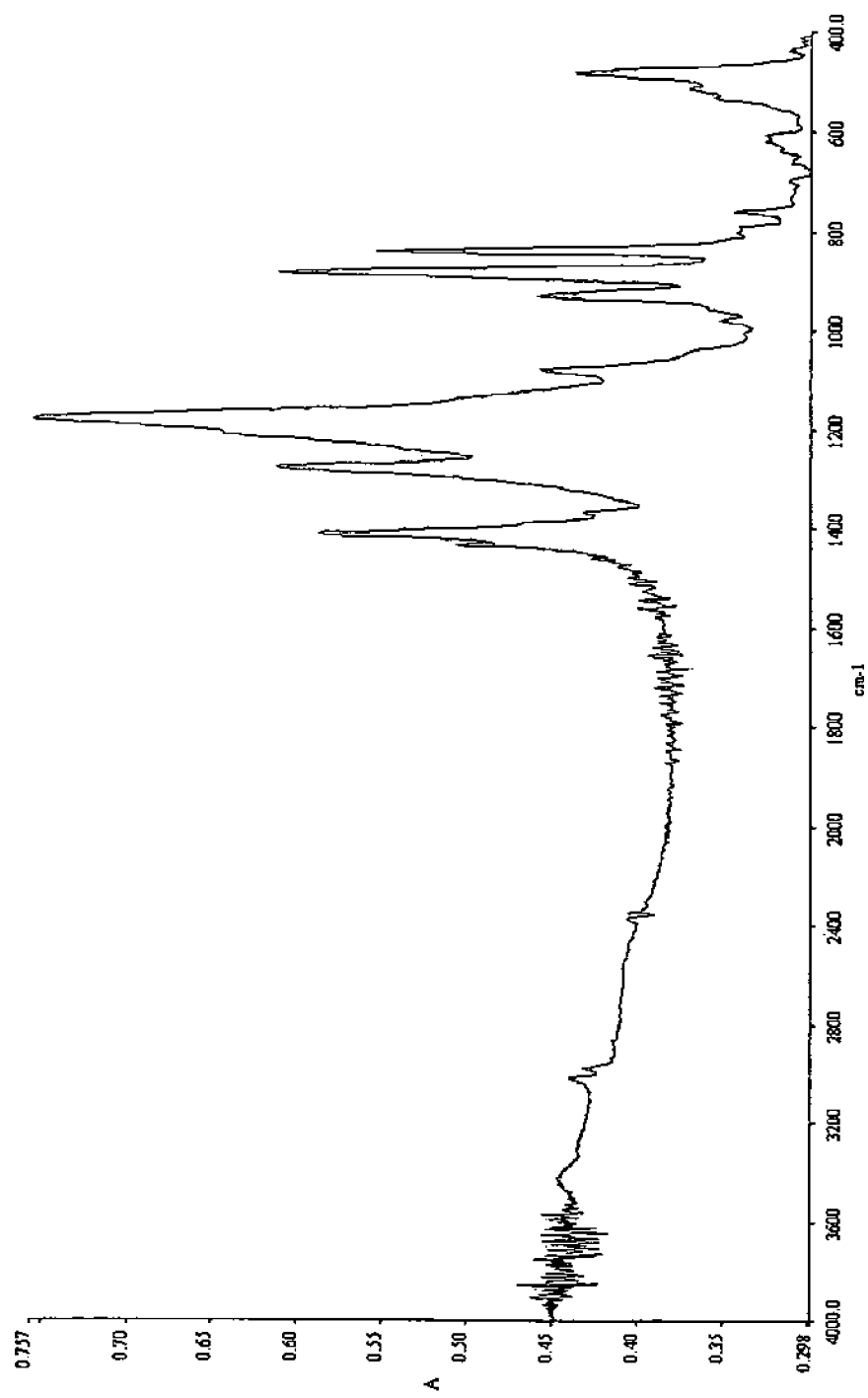
FIG. 9 is an IR chart of vinylidene fluoride homopolymer comprising a mixture of crystal forms I and H which is obtained in (3-1) of Preparation Example 3.

With respect to this VdF polymer, IR analysis was carried out. As a result, both of peaks which were characteristic to crystal forms I and II were recognized and it was confirmed that crystal form I and crystal form II were mixed. Further the calculated content (F(I)) of crystal form I was 79% by weight (cf. FIG. 9).

(3-2) Synthesis of $I(VdF)_n(CF_2CF_2)_2(VdF)_mI$ (n+m=10.4)

Into a 300 ml stainless steel autoclave equipped with a valve, pressure gauge and thermometer was poured 50 g of HCFC-225, and while cooling with a dry ice/methanol solution, 0.162 g of di-n-propylperoxy dicarbonate (50% by weight of methanol solution) was added and the inside of a system was sufficiently replaced with nitrogen gas. After the inside pressure of the system was reduced, 3.5 g of $I(CF_2CF_2)_2I$ was introduced through the valve, and after heating of the system up to 45° C., VdF was introduced until the inside pressure of the system became 0.8 MPaG. While maintaining the inside pressure and temperature of the system at 0.8 MPaG and 45° C., respectively, VdF was continuously introduced and 9-hour reaction was carried out.

After completion of the reaction, the inside temperature of the system was decreased to 25° C. and the unreacted substances (VdF and $I(CF_2CF_2)_2I$) were released. Then after the precipitated solid reaction product (VdF polymer) was taken out by filtration and washed with HCFC-225, the product was subjected to vacuum drying in a desiccator until a constant weight was reached to obtain 7.2 g of VdF polymer.

With respect to this VdF polymer, a degree (n+m) of polymerization obtained by $^{19}$F-NMR analysis was 10.4. Also Mw/Mn was 1.04.

With respect to this VdF polymer, IR analysis was carried out. As a result, both of peaks which were characteristic to crystal forms I and II were recognized and it was confirmed that crystal form I and crystal form II were mixed. Further the calculated content (F(I)) of crystal form I was 70% by weight.

Preparation Example 4

(4-1) Synthesis of $CF_3(VdF)_nC_2H_4I$ (n=8.1)

Into a 300 ml stainless steel autoclave equipped with a valve, pressure gauge and thermometer were poured 3 g of vinylidene fluoride oligomer (n=8.1) synthesized in (1-1) of Preparation Example, 30 g of ethyl acetate and 0.034 g of AIBN while the temperature inside a system was maintained at 25° C., and the inside of the system was sufficiently replaced with nitrogen gas. After reducing the inside pressure of the system and heating the system up to 65° C., ethylene gas was introduced until the inside pressure of the system became 0.7 MPaG. While maintaining the inside pressure and temperature of the system at 0.7 MPaG and 65° C., respectively, ethylene gas was continuously introduced and 5-hour reaction was carried out.

After completion of the reaction, the inside temperature of the system was decreased to 25° C. and the unreacted ethylene gas was released. Then the ethyl acetate solution in the system was poured into hexane and the precipitated solid reaction product (hereinafter referred to as "vinylidene fluoride oligomer/ethylene adduct") was taken out by filtration. The vinylidene fluoride oligomer/ethylene adduct was subjected to vacuum drying in a desiccator until a constant weight was reached, and 2.7 g of the adduct was obtained.

According to $^1$H-NMR and $^{19}$F-NMR analyses of this vinylidene fluoride oligomer/ethylene adduct, it was recognized that the peak around −38 ppm derived from the end —$CF_2I$ had been disappeared and peaks derived from the added ethylene were observed around 3.4 to 3.2 ppm and 2.8 to 2.6 ppm by $^1$H-NMR. In this case, an end modification ratio obtained by $^1$H-NMR was 95%.

According to IR analysis and powder X-ray diffraction analysis, only a peak which was characteristic to crystal form I was recognized and it was confirmed that the adduct was one having all-I-form crystal structure.

(4-2) Synthesis of $CF_3(VdF)_2C_2Hs$ (n=8.1)

Into a 50 ml four-necked flask equipped with a reflux condenser, thermometer, stirrer and dropping funnel were poured 30 ml of acetic acid, 0.5 g of vinylidene fluoride oligomer/ethylene adduct: $CF_3(VdF)_nC_2H_4I$ (n=8.1) synthesized in (4-1) of Preparation Example and 0.53 g of zinc powder, and 4-hour refluxing with heating was carried out.

After completion of the reaction, the inside temperature of a system was decreased to 25° C. and the zinc powder was removed by filtration. Then the reaction product, i.e. acetic acid solution was poured into pure water and the solid reaction product was taken out by re-precipitation. The solid reaction product was subjected to vacuum drying in a desiccator until a constant weight was reached, and 0.32 g of the product was obtained.

According to $^1$H-NMR analysis of this solid reaction product, it was recognized that the peaks derived from ethylene around 3.4 to 3.2 ppm and 2.8 to 2.6 ppm had been disappeared, the peak derived from the end methyl group was observed around 1.1 to 0.8 ppm, and the end iodine of the vinylidene fluoride oligomer/ethylene adduct had been converted to proton. In this case, an end modification ratio obtained by $^1$H-NMR was 96%.

According to IR analysis and powder X-ray diffraction analysis, only a peak which was characteristic to crystal form I was recognized and it was confirmed that the adduct was one having all-I-form crystal structure.

Example 1

Formation of Thin Film of VdF Polymer Having all-I-Form Crystal Structure by Spin Coating Method The $CF_3(VdF)_{10.1}I$ polymer having all-I-form crystal structure prepared in (1-3) of Preparation Example 1 was dissolved in acetone to make 3% by weight of acetone solution. The acetone solution was applied on an aluminum electrode at a rotation speed of 2,000 rpm by spin coating method to form a thin film, and then the solvent was distilled off in a desiccator. Thus a 200 nm thick thin film of VdF polymer having all-I-form crystal structure was formed.

The spin coating was carried out under the following condition by using the following equipment.
Coating Condition
  Number of revolutions: 2,000 rpm
Equipment
  MIKASA SPINCOATER 1H-D7 available from Mikasa Kabushiki Kaisha Example 2

Formation of Thin Film of VdF Polymer Having all-I-Form Crystal Structure by Vacuum Vapor Deposition Method A 200 nm thick thin film of VdF polymer having all-I-form crystal structure was formed on an aluminum electrode by vacuum vapor deposition method by using powder of $CF_3(VdF)_{10.1}I$ polymer having all-I-form crystal structure prepared in (1-3) of Preparation Example 1.

The vacuum vapor deposition was carried out under the following condition by using the following equipment.

Vapor Deposition Condition
  Substrate temperature: 25° C.
Equipment
  Organic thin film forming equipment available from Jyonan Kogyo Kabushiki Kaisha Example 3

Formation of Ferroelectric Thin Film of VdF Polymer

The vacuum vapor deposition of aluminum was carried out by usual method on the thin films of VdF polymer having all-I-form crystal structure which were formed on the aluminum electrodes in Examples 1 and 2, thereby forming second electrodes.

The obtained laminated articles were subjected to polarization under the following conditions.
Thin film temperature: 25° C.
Applied voltage: 200 MV/m
Treating time: 30 minutes With respect to the thin films of VdF polymer having all-I-form crystal structure subjected to polarization, electrical characteristics were evaluated, and as a result, the obtained D-E hysteresis curve showed a rectangular shape specific to ferroelectric materials.

According to the present invention, there can be provided a method of forming a thin film of vinylidene fluoride homopolymer having crystal form I which is applicable to various substrates in relatively easy way (coating conditions, application method, etc.).

Also according to the present invention, there can be provided a process for preparing a vinylidene fluoride homopolymer having crystal form I efficiently at high purity.

Further according to the present invention, there can be provided novel vinylidene fluoride homopolymers which can give a thin film being excellent in ferroelectricity.

What is claimed is:

1. A vinylidene fluoride homopolymer represented by the formula (4):

$$CF_3\text{-}(A^1)\text{-}I \quad (4)$$

wherein $A^1$ represents a structural unit of vinylidene fluoride homopolymer which comprises crystal form I alone or as main component and has a number average degree of polymerization of 5 to 12, wherein the vinylidene fluoride homopolymer comprises crystal form I alone or as main component and when attention is given to proportions of the respective vinylidene fluoride homopolymers having crystal form I, II or III which are calculated by IR analysis, the proportion of vinylidene fluoride homopolymers having crystal form I satisfies both of (Equation 3):

$$100 \geq \text{I-form}/(\text{I-form}+\text{II-form}) \geq 70\% \text{ by weight} \quad \text{(Equation 3)}$$

and (Equation 4):

$$100 \geq \text{I-form}/(\text{I-form}+\text{III-form}) \geq 70\% \text{ by weight} \quad \text{(Equation 4)}.$$

* * * * *